(12) United States Patent
Hara et al.

(10) Patent No.: US 8,513,448 B2
(45) Date of Patent: Aug. 20, 2013

(54) CYCLIC SILOXANE COMPOUND, A MATERIAL FOR FORMING SI-CONTAINING FILM, AND ITS USE

(75) Inventors: Daiji Hara, Yokohama (JP); Mayumi Takamori, Sagamihara (JP)

(73) Assignee: Tosoh Corporation, Yamaguchi (JP)

( * ) Notice: Subject to any disclaimer, the term of this patent is extended or adjusted under 35 U.S.C. 154(b) by 1443 days.

(21) Appl. No.: 11/815,194

(22) PCT Filed: Jan. 17, 2006

(86) PCT No.: PCT/JP2006/300519
§ 371 (c)(1),
(2), (4) Date: Jul. 31, 2007

(87) PCT Pub. No.: WO2006/080205
PCT Pub. Date: Aug. 3, 2006

(65) Prior Publication Data
US 2010/0052114 A1    Mar. 4, 2010

(30) Foreign Application Priority Data
Jan. 31, 2005    (JP) .................................. 2005-023256

(51) Int. Cl.
*C07F 7/00* (2006.01)

(52) U.S. Cl.
USPC ...................................................... 556/450

(58) Field of Classification Search
USPC .................. 556/460, 402, 410, 450, 451, 459
See application file for complete search history.

(56) References Cited

U.S. PATENT DOCUMENTS

| 3,132,117 | A  | 5/1964  | Schmidt |
| 3,876,677 | A  | 4/1975  | Wu |
| 2003/0078443 | A1 | 4/2003 | Lee et al. |
| 2004/0216641 | A1 | 11/2004 | Hamada et al. |
| 2005/0038220 | A1 | 2/2005 | Shin et al. |

FOREIGN PATENT DOCUMENTS

| EP | 575972 | * | 12/1993 |
| EP | 0990660 | A1 | 6/1998 |
| EP | 1143499 | A2 | 10/2001 |
| EP | 1493746 | A2 | 1/2005 |
| EP | 1249846 | A2 | 10/2005 |
| EP | 1583142 | A2 | 10/2005 |
| EP | 1698632 | A1 | 9/2006 |
| FR | 1437889 | A | 5/1966 |
| JP | 03-167228 | A | 7/1991 |
| JP | 05-086069 | A | 4/1993 |
| JP | 5-279856 | A | 10/1993 |
| JP | 6-177123 | A | 6/1994 |
| JP | 06-220328 | A | 8/1994 |
| JP | 7-101687 | B2 | 11/1995 |
| JP | 08-505363 | A | 6/1996 |
| JP | 10-114827 | A | 5/1998 |
| JP | 11-288931 | A | 10/1999 |
| JP | 2000-302791 | A | 10/2000 |
| JP | 2000-309753 | A | 11/2000 |
| JP | 2001-291713 | A | 10/2001 |
| JP | 2001-298023 | A | 10/2001 |
| JP | 2002-110670 | A | 4/2002 |
| JP | 2003-40998 | A | 2/2003 |
| JP | 2003-105088 | A | 4/2003 |
| JP | 2004-047873 | A | 2/2004 |
| JP | 3580403 | B2 | 7/2004 |
| JP | 2005-019980 | A | 1/2005 |
| JP | 2005-23075 | A | 1/2005 |
| JP | 2005-112853 | A | 4/2005 |
| JP | 2005-170943 | A | 6/2005 |
| JP | 2005-294333 | A | 10/2005 |
| WO | 03/019645 | A1 | 3/2003 |
| WO | 2004/027110 | A2 | 4/2004 |
| WO | 2004/049422 | A1 | 6/2004 |
| WO | 2006/080205 | A1 | 8/2006 |

OTHER PUBLICATIONS

Okawa et al. for EP 575972, STN Printout Acession No. 1994:437424.*
Austrian Office Action dated Oct. 31, 2008.
Database Beilstein; Beilstein Institute for Organic Chemistry, Frankfurt-Main, DE; 1989, XP002300739. retrieved from xfire accession No. BRN 1794950.
Database Beilstein; Beilstein Institute for Organic Chemistry, Frankfurt-Main, DE; 1989, XP002300741 retrieved from xfire accession No. BRN 2397618.
Database Beilstein; Beilstein Institute for Organic Chemistry, Frankfurt-Main, DE; 1993 XP002300742 retrieved from xfire accession No. BRN 5582607.
Database Beilstein; Beilstein Institute for Organic Chemistry, Frankfurt-Main, DE; 1993, XP002300743, retrieved from xfire accession No. BRN 5641308; & Lavrent'ev V.I. et. al.: Gen. Chem. USSR (Engl.Transl.), vol. 50, No. 2, 1980, pp. 312-317.

(Continued)

*Primary Examiner* — Johann R Richter
*Assistant Examiner* — Jennifer C Sawyer
(74) *Attorney, Agent, or Firm* — Sughrue Mion, PLLC (57) ABSTRACT

The present invention has the objects to provide a novel material for forming Si-containing film, especially a material containing a cyclic siloxane compound suitable to a PECVD equipment for low dielectric constant insulating film, and to provide an Si-containing film using the same, and a semiconductor device containing those films. The present invention relates to a material for forming Si-containing film, containing a cyclic siloxane compound represented by the following general formula (1)

[Chem. 1] (1)

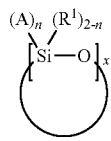

(In the formula, A represents a group containing at least one selected from the group consisting of an oxygen atom, a boron atom and a nitrogen atom, n is 1 or 2, and x is an integer of from 2 to 10.), and its use.

13 Claims, 2 Drawing Sheets

(56) References Cited

OTHER PUBLICATIONS

Crandall J K et al: "Siloxanes from the hydrolysis of isopropyltrimethoxysilane" Journal of Organometallic Chemistry, Elsevier-Sequoia S.A. Lausanne, CH, vol. 489, No. 1, Mar. 8, 1995, pp. 5-13, XP004024184; ISSN: 0022-328X.
Okawara R et al: "Alkylalkoxypolysiloxanes. VI. Lower Members of Cyclic Methyl-, and Ethyl-Ethoxypolysiloxanes" Bulletin of the Chemical Society of Japan, Chemical Society of Japan, Tokyo, JP, vol. 31, No. 1, Jan. 1, 1958, pp. 22-25, XP009048486; ISSN: 0009-2673.
Okawara R et al: "Alkylalkoxypolysiloxanes. VIII. Lower Members of Cyclic Methyl- and Ethyl-Isopropoxypolysiloxanes" Bulletin of the Chemical Society of Japan, Chemical Society of Japan, Tokyo, JP, vol. 33, No. 5, May 1, 1960, p. 659/660, XP009048487; ISSN 0009-2673.
Sprung M M et al: "The Partial Hydrolysis of Methyltrimethoxysilane" Journal of the American Chemical Society, American Chemical Society, New York, USA, vol. 77, Aug. 5, 1955, pp. 4173-4175, XP001206395, ISSN: 0002-7863.
Extended European Search Report dated Apr. 29, 2010, issued in counterpart Application No. 06711799.4-2117.
Office Action issued in counterpart Chinese Application No. 2006800037264 dated Feb. 5, 2010.
Extended European Search Report issued on May 10, 2011 in the corresponding European Patent Application No. 10176573.3.
Office Action dated May 4, 2011 from the Taiwanese Patent Office in counterpart Taiwanese application No. 095103485.
European Search Report issued on Oct. 22, 2010 in the corresponding European Patent Application No. 10176573.3.
Office Action dated Nov. 16, 2010, issued in corresponding Japanese application No. JP 2005-349432.
Japanese Office Action issued in Application No. 2005-349432, issued on Jul. 27, 2010.
Notice of Appeal Board's Decision; dated Nov. 22, 2011; issued by the Japanese Patent Office in corresponding Japanese Patent Application No. 2005-349432.
European Office Action issued on Nov. 9, 2011 by the European Patent Office in corresponding European Patent Application No. 10176573.3.
Korean Office Action issued in corresponding Appln. No. 10-2007-7019050 dated Jan. 16, 2012.
Communication issued on Jan. 20, 2012 by the Intellectual Property Office of the P.R. of China in the corresponding Chinese Patent Application No. 200680003726.4.
Office Action Issued on Apr. 9, 2012 in corresponding Taiwanese Application No. 095103485.
Communication issued Aug. 3, 2012 by The Intellectual Property Office of the People's Republic of China in counterpart Chinese Application No. 200680003726.4.
Communication, dated Oct. 26, 2012, issued by the Korean Intellectual Property Office in counterpart Korean Application No. 10-2007-7019050.
Office Action, dated May 7, 2013, issued by the Japanese Patent Office in counterpart Japanese Patent Application No. 2010-207028.

\* cited by examiner

CYCLIC SILOXANE COMPOUND, A MATERIAL FOR FORMING SI-CONTAINING FILM, AND ITS USE

TECHNICAL FIELD

The present invention relates to a material for forming Si-containing film and the like, and particularly to a material for a low dielectric constant interlayer insulating film used in multilayer interconnect technology in logic ULSI. Especially, it relates to a material for forming Si-containing film containing a cyclic siloxane compound for plasma polymerization and its use.

BACKGROUND ART

In production technology in the field of integrated circuit in an electronic industries, demand for high integration and speed-up is increasing. With respect to silicon ULSI, especially logic ULSI, rather than performance by miniaturization of MOSFET, performance of wiring connecting those has been problematic. Namely, reduction in wiring resistance and reduction in capacitance between wirings and in interlayer capacitance are required in order to solve the problem in wiring delay due to multilayer interconnects.

Accordingly, at present, instead of aluminum wiring used for the most part of the in integrated circuit, introduction of copper wiring having a lower electric resistance and migration resistance is essential, and a process of conducting copper plating after seed formation by sputtering or chemical vapor deposition (hereinafter abbreviated as CVD) method has been used practically.

There are various proposals as a low dielectric constant interlayer insulating film material. Heretofore as the inorganic system, silicon dioxide ($SiO_2$), silicon nitride and a phosphosilicate glass have been used, and as the organic system a polyimide has been used. However, recently, with a purpose of obtaining a more homogenous interlayer insulating film, there are the proposal of previously hydrolyzing, that is, polycondensing, a tetraethoxysilane monomer to obtain $SiO_2$, and using as a coating material called inorganic Spin on Glass (inorganic SOG), and the proposal of using a polysiloxane obtained by polycondensing an organic alkoxysilane monomer, as an organic SOG.

Further, as a method of forming the insulating film, there are the following two methods. An application method of a coating method of coating an insulating film polymer solution with a spin coat or the like to form a film, and a CVD method of mainly plasma polymerizing in a plasma enhanced chemical vapor deposition (PECVD) equipment to form a film.

As the proposal of the PECVD method, for example, Patent Document 1 proposes a method of forming a trimethylsilane oxide thin film from trimethylsilane and oxygen by the PECVD method, and Patent Document 2 proposes a method of forming an alkylsilane oxide thin film from an alkoxysilane having a straight-chain alkyl such as methyl, ethyl and n-propyl, an alkynyl such as vinyl, phenyl, and an aryl group by the PECVD method. Those insulating films formed with the conventional PECVD method materials have good adhesion to a barrier metal and a copper wiring material which is a wiring material, whereas there were the cases that uniformity of a film becomes problem and film formation rate and dielectric constant are insufficient.

As the proposal of PECVD using a cyclic siloxane, Patent Document 3 proposes a method of using tetramethylcyclotetrasiloxane, and Patent Document 4 proposes a method of using tetraalkylcyclotetrasiloxane, tetraminocyclotetrasiloxane, octaalkylcyclotetrasiloxane or octaminocyclotetrasiloxane. Those methods intend to lower dielectric constant by using a cyclic siloxane as a raw material compound to form pores in a thin film formed, while maintaining its cyclic structure in the thin film formed. However, according to the present inventors' finding, when a film is formed by PECVD using those substituted cyclic siloxanes, a thin film having dielectric constant of less than 2.7 is not obtained. This is considered due to that a cyclic structure of its cyclic siloxane compound is easily disintegrated in plasma to form a chain structure, and thus does not contribute to make a porous thin film.

Further, Patent Document 5 proposes a six-membered cyclic siloxane such as hexamethylcyclotrisiloxane and 1,3,5-trimethyl-1,3,5-trivinylcyclotrisiloxane, and Patent Document 6 proposes to copolymerize a bisbenzocyclobutene-substituted disiloxane compound and 1,3,5,7-tetramethyl-1,3,5,7-tetravinylcyclotetrasiloxane as an eight-membered cyclic siloxane under a plasma condition. However, according to the present inventors' finding, a thin film having dielectric constant of less than 2.5 is not obtained by a method of using vinyl- and/or methyl-substituted cyclic siloxane as proposed by those.

Patent Document 7 and Patent Document 8 propose a film formation method of a low dielectric constant thin film by PECVD method using a porogene. The former proposes a method of lowering dielectric constant by feeding triethoxysilane, diethoxymethylsilane and α-terpinene as a porogene in PECVD equipment chamber, forming PECVD film, and annealing at a temperature of 400° C. or higher to vaporize a component derived from α-terpinene in a thin film, thereby making the thin film porous. The latter proposes a method of lowering dielectric constant by supplying cyclo-1,3,5,7-tetrasilylene-2,6-dioxy-4,8-dimethylene, vinylfuryl ether as porogene, and nitrous oxide as an oxidizing agent in PECVD equipment chamber, forming PECVD film, annealing at a temperature of 400° C. or higher, and vaporizing a component derived from vinylfuryl ether in a thin film, thereby making the thin film porous. Those methods can expect to lower dielectric constant by pore formation. However, the component derived from porogene is removed from the inside of the thin film once formed, into the outside thereof by a post-treatment. Therefore, there are the problems that matrix of the thin film is disintegrated, a composition in the inside of the film becomes heterogenous, mechanical strength such as hardness and Young modulus deteriorates, pores formed become a continuous open pore, and diffusion of a metal component into a film is not prevented.

On the other hand, as the proposal of coating type, although uniformity of a film is good, three steps of coating, solvent removal and heat treatment are necessary, and this is economically disadvantageous than CVD material. Further, there are many cases that adhesion to a barrier metal and a copper wiring material as a wiring material, and uniform coating of a coating liquid to a miniaturized substrate structure become the problem.

Further, in the coating type material, a method of forming a porous material in order to form Ultra Low-k material having dielectric constant of 2.5 or lower, and further 2.0 or lower is proposed. There are a method of forming pores by dispersing organic component fine particles which are easily thermally decomposed, in a matrix of an organic or inorganic material, and heat treating; a method of forming $SiO_2$ ultrafine particle thin film by evaporating silicon and oxygen in a gas to deposit $SiO_2$ ultrafine particles formed; and the like. However, those pore forming methods are effective to lower dielectric constant, but there were the cases that mechanical property deteriorates, Chemical Mechanical Polishing (CMP) becomes difficult, and water adsorption gives rises to heighten of a dielectric constant and wiring corrosion due to adsorption of moisture.

Therefore, the market further requires materials having good balance satisfying all of the requirements of low dielectric constant, sufficient mechanical strength, adhesion to a barrier metal, prevention of copper diffusion, plasma ashing resistance, moisture resistance and the like. As a method of satisfying those requirements with good balance in a certain degree, a material is proposed which has intermediate properties between an organic polymer and an inorganic polymer by increasing carbon proportion of organic substituents to silane in an organic silane material. For example, Patent Document 9 proposes a method of obtaining an interlayer insulating film having dielectric constant of 2.4 or less using a coating solution obtained by hydrolytically polycondensing a silicon compound having an adamantyl group in the presence of an acidic aqueous solution by a sol-gel method, without forming pores. However, this material is a coating type material, and still has the problem of the film forming method by a coating type as described above.

Patent Document 1: JP-A-2002-110670
Patent Document 2: JP-A-11-288931
Patent Document 3: Japanese Patent No 2067801
Patent Document 4: JP-A-5-279856
Patent Document 5: WO 03/019645 pamphlet
Patent Document 6: JP-A-2004-47873
Patent Document 7: JP-A-2005-19980
Patent Document 8: JP-A-2001-298023
Patent Document 9: JP-A-2000-302791

DISCLOSURE OF THE INVENTION

Problems that the Invention is to Solve

The present invention has been made in view of the above problems, and its object is to provide a material for forming novel Si-containing film, especially a material containing a cyclic siloxane compound suitable to a PECVD equipment for low dielectric constant insulating film, and to provide an Si-containing film using the same, and a semiconductor device containing those films.

Means for Solving the Problems

The present inventors have found that a cyclic siloxane compound having a substituent containing a hetero atom is suitable as an insulating film, especially a low dielectric constant interlayer insulating film material for a semiconductor device, and accomplished the present invention.

That is, the present invention relates to a material for forming Si-containing film, characterized by containing a cyclic siloxane compound represented by the following general formula (1)

[Chem. 1]

(1)

(In the formula, A represents a group containing at least one selected from the group consisting of an oxygen atom, a boron atom and a nitrogen atom, and $R^1$ represents a hydrogen atom or a hydrocarbon group. n is 1 or 2, and x is an integer of from 2 to 10.).

Further, the present invention resides in a production method of an Si-containing film, characterized by using the above-described material for forming Si-containing film as a raw material. Further, the present invention relates to an Si-containing film, characterized by being obtained by the above-described method. Further, the present invention resides in a production method of an Si-containing film, characterized by subjecting the above-described Si-containing film to heat treatment, ultraviolet irradiation treatment or electron ray treatment. Further, the present invention resides in an Si-containing film, characterized by being obtained by the above-described production method. Further, the present invention resides in a semiconductor device, characterized by using the above-described Si-containing film as an insulating film.

Further, the present invention resides in a cyclic siloxane compound, characterized by being represented by the following general formula (20)

[Chem. 2]

(20)

(In the formula, $R^{18}$ represents a hydrocarbon group, and $R^{19}$ represents a hydrogen atom or a hydrocarbon group. g is an integer of from 2 to 10, and h is an integer of from 1 to 3.).

ADVANTAGE OF THE INVENTION

According to the present invention, the following remarkable effects are exhibited. That is, as a first advantage of the present invention, a material having a low dielectric constant and high mechanical strength can be provided as a low dielectric constant material in an interlayer insulating film of a semiconductor device, by using the cyclic siloxane compound represented by the general formula (1) as a material for forming Si-containing film. Further, the present invention can produce a cyclic siloxane compound represented by the general formula (1) which is useful as a PECVD method interlayer insulating film material in high purity with good efficiency.

DESCRIPTION OF REFERENCE NUMERALS AND SIGNS

1. PECVD equipment
2. PECVD chamber
3. Upper electrode
4. Lower electrode
5. Substrate for forming thin film
6. Matching circuit
7. RF power source
8. Temperature control equipment
9. Vaporizer
10. Liquid flow rate control equipment
11. Gas flow rate control equipment
12. Container
13. Compound represented by the general formula (1)
14. Piping
15. Piping
16. Exhaust equipment
17. Earth ground
18. Earth ground
19. PECVD equipment
20. PECVD chamber 21. Coil
22. Quartz pipe
23. Heater part
24. Substrate for forming thin film
25. Matching circuit
26. RF power source
27. Temperature control equipment
28. Vaporizer
29. Liquid flow rate control equipment
30. Gas flow rate control equipment
31. Shower head
32. Container
33. Compound represented by the general formula (1)
34. Piping
35. Piping
36. Exhaust equipment
37. Earth ground

BEST MODE FOR CARRYING OUT THE INVENTION

The present invention is described in detail below.

In the present invention, a hydrocarbon group shown by $R^1$, and $R^2$, $R^4$, $R^6$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$ shown hereinafter is preferably a saturated or unsaturated hydrocarbon group, and may have any of straight-chain, branched-chain and cyclic structures. Further, in the general formulae (3), (5) and (7) shown below, when p, q or r is 2 or more, the respective formulae may be bonded with each other to form a cyclic structure. Where the number of carbon atoms exceeds 20, it may be difficult to get a raw material such as the corresponding organic halide, and even if got, its purity may be low. Further, where considering stable use in a CVD equipment, a hydrocarbon group having from 1 to 6 carbon atoms is particularly preferable in the point that vapor pressure of an organic silane does not become too low.

The hydrocarbon group shown by $R^1$, and $R^2$, $R^4$, $R^6$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ shown hereinafter is not particularly limited, but is preferably an alkyl group having from 1 to 6 carbon atoms, an aryl group, an arylalkyl group, an alkylaryl group, an alkenyl group, an arylalkenyl group, an alkenylaryl group, an alkynyl group, an arylalkynyl group and an alkynylaryl group, and more preferably an alkyl group having from 1 to carbon atoms and an aryl group.

Specific example include alkyl groups such as methyl, ethyl, n-propyl, i-propyl, cyclopropyl, n-butyl, i-butyl, sec-butyl, tert-butyl, cyclobutyl, n-pentyl, tert-amyl, cyclopentyl, n-hexyl, cyclohexyl and 2-ethylhexyl; aryl groups such as phenyl, diphenyl and naphthyl; arylalkyl groups such as benzyl and methylbenzyl; and alkylaryl groups such as o-toluoyl, m-toluoyl, p-toluoyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,6-trimethylphenyl, o-ethylphenyl, m-ethylphenyl and p-ethylphenyl.

Further examples include alkenyl groups such as vinyl, allyl, 1-propenyl, 1-butenyl, 1,3-butadienyl, 1-pentenyl, 1-cyclopentenyl, 2-cyclopentenyl, cyclopentadienyl, methylcyclopentadienyl, ethylcyclopentadienyl, 1-hexenyl, 1-cyclohexenyl, 2,4-cyclohexadienyl, 2,5-cyclohexadienyl, 2,4,6-cycloheptatrienyl and 5-norbornen-2-yl; arylalkenyl groups such as 2-phenyl-1-ethenyl; alkenylaryl groups such as o-styryl, m-styryl and p-styryl; alkynyl groups such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl and 5-hexynyl; arylalkynyl groups such as 2-phenyl-1-ethynyl; and alkynylaryl groups such as 2-ethynyl-2-phenyl.

Of those, an alkyl group having from 1 to 4 carbon atoms and phenyl group are particularly preferable.

In the above general formula (1), A represents a group containing at least one selected from the group consisting of an oxygen atom, a boron atom and a nitrogen atom, and may have any of straight-chain, branched-chain and cyclic structures.

Above all, A containing oxygen is preferable, and the example thereof includes an oxygen-containing group represented by the following general formula (2)

[Chem. 3]

$$—O—R^2 \qquad (2)$$

(In the formula, $R^2$ are the same as defined above), or the following general formula (3)

[Chem. 4]

$$—R^3—(—O—R^2)_p \qquad (3)$$

(In the formula, $R^2$ are the same as defined above, $R^3$ represents a hydrocarbon residue. p is the number of $OR^2$ as a substituent on $R^3$, and is an integer of 1 or more.).

Examples of $R^3$ in the above general formula (3), and $R^5$ and $R^7$ shown hereinafter include hydrocarbon residues having structures in which p, q or r hydrogen atoms are eliminated from the structures of hydrocarbon groups shown as the examples of $R^1$, $R^2$, $R^4$, $R^6$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$, respectively. A saturated or unsaturated hydrocarbon residue having from 1 to 20 carbon atoms is preferable, and may have any of straight-chain, branched-chain and cyclic structures.

Where the number of carbon atoms exceeds 20, vapor pressure of an organic silane formed becomes low, and it may be difficult to use in a PECVD equipment, resulting in an unfavorable case. The A containing oxygen is preferably an alkoxy group, a silanoxy group, an alkoxyaryl group or an alkoxyalkyl group, and more preferably an alkoxy group having from 1 to 4 carbon atoms, a phenyl group which has an alkoxy group having from 1 to 4 carbon atoms as a substituent, or an alkyl group having from 1 to 4 carbon atoms which has an alkoxy group having from 1 to 4 carbon atoms as a substituent. $R^1$ in this case is preferably an alkyl group having from 1 to 6 carbon atoms, and more preferably an alkyl group having from 1 to 4 carbon atoms.

Example of the A containing nitrogen includes a nitrogen-containing group represented by the following general formula (4)

[Chem. 5]

(4)

(In the formula, $R^4$ is the same as defined above), or the following general formula (5)

[Chem. 6]

(5)

(In the formula, $R^4$ is the same as defined above. $R^5$ represents a hydrocarbon residue. q is the number of $NR^4_2$ as a substituent on $R^5$, and is an integer of 1 or more.). In the above formula, $R^4$s may be the same or different. The A containing nitrogen is preferably an alkylamino group, a dialkylamino group, an arylamino group or a diarylamino group.

Example of the A containing boron include a boron-containing group represented by the following general formula (6)

[Chem. 7]

(6)

(In the formula, $R^6$ is the same as defined above), or the following general formula (7)

[Chem. 8]

(7)

(In the formula, $R^6$ is the same as defined above. $R^7$ represents a hydrocarbon residue. r is the number of $BR^6{}_2$ substituted on $R^7$, and is an integer of 1 or more.). In the above formula, $R^6$s may be the same or different. The A containing boron is preferably an alkylboron residue or an alkoxyboron residue.

Further, a material for forming Si-containing film, characterized by containing a cyclic siloxane compound represented by the general formula (1) having a structure that substituents of the general formulae (2) to (7) are present as a mixture is included in the scope of the present invention.

In the general formula (1), when $R^1$ is a secondary hydrocarbon group or a tertiary hydrocarbon group, directly bonded to Si atom, the cyclic siloxane compound represented by the general formula (1) is stabilized in plasma, and a thin film having a low dielectric constant value and high mechanical properties is obtained, which is preferable. Further, n is preferably 1, x is preferably 3 to 4, and a molecular weight of the cyclic siloxane compound represented by the general formula (1) is preferably less than 1,000.

Specific examples of the cyclic siloxane compound represented by the general formula (1) include 2,4,6-tritert-butyl-2,4,6-trimethoxycyclotrisiloxane, 2,4,6-trisec-butyl-2,4,6-trimethoxycyclotrisiloxane, 2,4,6-triisobutyl-2,4,6-trimethoxycyclotrisiloxane, 2,4,6-tri-n-butyl-2,4,6-trimethoxycyclotrisiloxane, 2,4,6-tricyclobutyl-2,4,6-trimethoxycyclotrisiloxane, 2,4,6-triisopropyl-2,4,6-trimethoxycyclotrisiloxane, 2,4,6-tri-n-propyl-2,4,6-trimethoxycyclotrisiloxane, 2,4,6-tricyclopropyl-2,4,6-trimethoxycyclotrisiloxane, 2,4,6-triethyl-2,4,6-trimethoxycyclotrisiloxane and 2,4,6-trimethyl-2,4,6-trimethoxycyclotrisiloxane.

Further examples include 2,4,6-tritert-butyl-2,4,6-triethoxycyclotrisiloxane, 2,4,6-trisec-butyl-2,4,6-triethoxycyclotrisiloxane, 2,4,6-triisobutyl-2,4,6-triethoxycyclotrisiloxane, 2,4,6-tri-n-butyl-2,4,6-triethoxycyclotrisiloxane, 2,4,6-tricyclobutyl-2,4,6-triethoxycyclotrisiloxane, 2,4,6-triisopropyl-2,4,6-triethoxycyclotrisiloxane, 2,4,6-tri-n-propyl-2,4,6-triethoxycyclotrisiloxane, 2,4,6-tricyclopropyl-2,4,6-triethoxycyclotrisiloxane, 2,4,6-triethyl-2,4,6-triethoxycyclotrisiloxane and 2,4,6-trimethyl-2,4,6-triethoxycyclotrisiloxane.

Further examples include 2,4,6-tritert-butyl-2,4,6-tri-n-propoxycyclotrisiloxane, 2,4,6-trisec-butyl-2,4,6-tri-n-propoxycyclotrisiloxane, 2,4,6-triisobutyl-2,4,6-tri-n-propoxycyclotrisiloxane, 2,4,6-tri-n-butyl-2,4,6-tri-n-propoxycyclotrisiloxane, 2,4,6-tricyclobutyl-2,4,6-tri-n-propoxycyclotrisiloxane, 2,4,6-triisopropyl-2,4,6-tri-n-propoxycyclotrisiloxane, 2,4,6-tri-n-propyl-2,4,6-tri-n-propoxycyclotrisiloxane, 2,4,6-tricyclopropyl-2,4,6-tri-n-propoxycyclotrisiloxane, 1,3,5-triethyl-1,3,5-tri-n-propoxycyclotrisiloxane and 2,4,6-trimethyl-2,4,6-tri-n-propoxycyclotrisiloxane.

Further examples include 2,4,6-tritert-butyl-2,4,6-triisopropoxycyclotrisiloxane, 2,4,6-trisec-butyl-2,4,6-triisopropoxycyclotrisiloxane, 2,4,6-triisobutyl-2,4,6-triisopropoxycyclotrisiloxane, 2,4,6-tri-n-butyl-2,4,6-triisopropoxycyclotrisiloxane, 2,4,6-tricyclobutyl-2,4,6-triisopropoxycyclotrisiloxane, 2,4,6-triisopropyl-2,4,6-triisopropoxycyclotrisiloxane, 2,4,6-tri-n-propyl-2,4,6-triisopropoxycyclotrisiloxane, 2,4,6-tricyclopropyl-2,4,6-triisopropoxycyclotrisiloxane, 2,4,6-triethyl-2,4,6-triisopropoxycyclotrisiloxane and 2,4,6-trimethyl-2,4,6-triisopropoxycyclotrisiloxane.

Further examples include 2,4,6,8-tetratert-butyl-2,4,6,8-tetramethoxycyclotetrasiloxane, 2,4,6,8-tetrasecbutyl-2,4,6,8-tetramethoxycyclotetrasiloxane, 2,4,6,8-tetraisobutyl-2,4,6,8-tetramethoxycyclotetrasiloxane, 2,4,6,8-tetra-n-butyl-2,4,6,8-tetramethoxycyclotetrasiloxane, 2,4,6,8-tetracyclobutyl-2,4,6,8-tetramethoxycyclotetrasiloxane, 2,4,6,8-tetraisopropyl-2,4,6,8-tetramethoxycyclotetrasiloxane, 2,4,6,8-tetra-n-propyl-2,4,6,8-tetramethoxycyclotetrasiloxane, 2,4,6,8-tetracyclopropyl-2,4,6,8-tetramethoxycyclotetrasiloxane, 2,4,6,8-tetraethyl-2,4,6,8-tetramethoxycyclotetrasiloxane and 2,4,6,8-tetramethyl-2,4,6,8-tetramethoxycyclotetrasiloxane.

Further examples include 2,4,6,8-tetratert-butyl-2,4,6,8-tetraethoxycyclotetrasiloxane, 2,4,6,8-tetrasecbutyl-2,4,6,8-tetraethoxycyclotetrasiloxane, 2,4,6,8-tetraisobutyl-2,4,6,8-tetraethoxycyclotetrasiloxane, 2,4,6,8-tetra-n-butyl-2,4,6,8-tetraethoxycyclotetrasiloxane, 2,4,6,8-tetracyclobutyl-2,4,6,8-tetraethoxycyclotetrasiloxane, 2,4,6,8-tetraisopropyl-2,4,6,8-tetraethoxycyclotetrasiloxane, 2,4,6,8-tetra-n-propyl-2,4,6,8-tetraethoxycyclotetrasiloxane, 2,4,6,8-tetracyclopropyl-2,4,6,8-tetraethoxycyclotetrasiloxane, 2,4,6,8-tetraethyl-2,4,6,8-tetraethoxycyclotetrasiloxane and 2,4,6,8-tetramethyl-2,4,6,8-tetraethoxycyclotetrasiloxane.

Further examples include 2,4,6,8-tetratert-butyl-2,4,6,8-tetra-n-propoxycyclotetrasiloxane, 2,4,6,8-tetrasec-butyl-2,4,6,8-tetra-n-propoxycyclotetrasiloxane, 2,4,6,8-tetraisobutyl-2,4,6,8-tetra-n-propoxycyclotetrasiloxane, 2,4,6,8-tetra-n-butyl-2,4,6,8-tetra-n-propoxycyclotetrasiloxane, 2,4,6,8-tetracyclobutyl-2,4,6,8-tetra-n-propoxycyclotetrasiloxane, 2,4,6,8-tetraisopropyl-2,4,6,8-tetra-n-propoxycyclotetrasiloxane, 2,4,6,8-tetra-n-propyl-2,4,6,8-tetra-n-propoxycyclotetrasiloxane, 2,4,6,8-tetracyclopropyl-2,4,6,8-tetra-n-propoxycyclotetrasiloxane, 2,4,6,8-tetraethyl-2,4,6,8-tetra-n-propoxycyclotetrasiloxane and 2,4,6,8-tetramethyl-2,4,6,8-tetra-n-propoxycyclotetrasiloxane.

Further examples include 2,4,6,8-tetratert-butyl-2,4,6,8-tetraisopropoxycyclotetrasiloxane, 2,4,6,8-tetrasec-butyl-2,4,6,8-tetraisopropoxycyclotetrasiloxane, 2,4,6,8-tetraisobutyl-2,4,6,8-tetraisopropoxycyclotetrasiloxane, 2,4,6,8-tetra-n-butyl-2,4,6,8-tetraisopropoxycyclotetrasiloxane, 2,4,6,8-tetracyclobutyl-2,4,6,8-tetraisopropoxycyclotetrasiloxane, 2,4,6,8-tetraisopropyl-2,4,6,8-tetraisopropoxycyclotetrasiloxane, 2,4,6,8-tetra-n-propyl-2,4,6,8-tetraisopropoxycyclotetrasiloxane, 2,4,6,8-tetracyclopropyl-2,4,6,8-tetraisopropoxycyclotetrasiloxane, 2,4,6,8-tetraethyl-2,4,6,8- tetraisopropoxycyclotetrasiloxane and 2,4,6,8-tetramethyl-2, 4,6,8-tetraisopropoxycyclotetrasiloxane.

Further examples include 2,4,6,8,10-pentatert-butyl-2,4,6, 8,10-pentamethoxycyclopentasiloxane, 2,4,6,8,10-pentasec-butyl-2,4,6,8,10-pentamethoxycyclopentasiloxane, 2,4,6,8, 10-pentaisobutyl-2,4,6,8,10-pentamethoxycyclopentasiloxane, 2,4,6,8,10-penta-n-butyl-2,4,6,8,10-pentamethoxycyclopentasiloxane, 2,4,6,8,10-pentacyclobutyl-2,4,6,8,10-pentamethoxycyclopentasiloxane, 2,4,6,8,10-pentaisopropyl-2,4,6,8,10-pentamethoxycyclopentasiloxane, 2,4,6,8,10-penta-n-propyl-2,4,6,8,10-pentamethoxycyclopentasiloxane, 2,4,6,8, 10-pentacyclopropyl-2,4,6,8,10-pentamethoxycyclopentasiloxane, 2,4,6,8,10-pentaethyl-2, 4,6,8,10-pentamethoxycyclopentasiloxane and 2,4,6,8,10-pentamethyl-2,4,6,8,10-pentamethoxycyclopentasiloxane.

Further examples include 2,4,6,8,10-pentatert-butyl-2,4,6, 8,10-pentaethoxycyclopentasiloxane, 2,4,6,8,10-pentasec-butyl-2,4,6,8,10-pentaethoxycyclopentasiloxane, 2,4,6,8,10-pentaisobutyl-2,4,6,8,10-pentaethoxycyclopentasiloxane, 2,4,6,8,10-penta-n-butyl-2,4,6,8,10-pentaethoxycyclopentasiloxane, 2,4,6,8,10-pentacyclobutyl-2,4,6,8,10-pentaethoxycyclopentasiloxane, 2,4,6,8,10-pentaisopropyl-2,4,6, 8,10-pentaethoxycyclopentasiloxane, 2,4,6,8,10-pent-n-propyl-2,4,6,8,10-pentaethoxycyclopentasiloxane, 2,4,6,8, 10-pentacyclopropyl-2,4,6,8,10-pentaethoxycyclopentasiloxane, 2,4,6,8,10-pentaethyl-2,4, 6,8,10-pentaethoxycyclopentasiloxane and 2,4,6,8,10-pentamethyl-2,4,6,8,10-pentaethoxycyclopentasiloxane.

Further examples include 2,4,6,8,10-pentatert-butyl-2,4,6, 8,10-penta-n-propoxycyclopentasiloxane, 2,4,6,8,10-pentasec-butyl-2,4,6,8,10-penta-n-propoxycyclopentasiloxane, 2,4,6,8,10-pentaisobutyl-2,4,6,8,10-penta-n-propoxycyclopentasiloxane, 2,4,6,8,10-penta-n-butyl-2,4,6,8,10-penta-n-propoxycyclopentasiloxane, 2,4,6,8,10-pentacyclobutyl-2,4, 6,8,10-penta-n-propoxycyclopentasiloxane, 2,4,6,8,10-pentaisopropyl-2,4,6,8,10-penta-n-propoxycyclopentasiloxane, 2,4,6,8,10-penta-n-propyl-2,4, 6,8,10-penta-n-propoxycyclopentasiloxane, 2,4,6,8,10-pentacyclopropyl-2,4,6,8,10-penta-n-propoxycyclopentasiloxane, 2,4,6,8,10-pentaethyl-2,4,6,8, 10-penta-n-propoxycyclopentasiloxane and 2,4,6,8,10-pentamethyl-2,4,6,8,10-penta-n-propoxycyclopentasiloxane.

Further examples include 2,4,6,8,10-pentatert-butyl-2,4,6, 8,10-pentaisopropoxycyclo-pentasiloxane, 2,4,6,8,10-pentasec-butyl-2,4,6,8,10-pentaisopropoxycyclopentasiloxane, 2,4,6,8,10-pentaisobutyl-2,4,6,8,10-pentaisopropoxycyclopentasiloxane, 2,4,6,8,10-penta-n-butyl-2,4,6,8,10-pentaisopropoxycyclopentasiloxane, 2,4,6,8,10-pentacyclobutyl-2,4, 6,8,10-pentaisopropoxycyclopentasiloxane, 2,4,6,8,10-pentaisopropyl-2,4,6,8,10-pentaisopropoxycyclopentasiloxane, 2,4,6,8,10-penta-n-propyl-2,4,6,8,10-pentaisopropoxycyclopentasiloxane, 2,4, 6,8,10-pentacyclopropyl-2,4,6,8,10-pentaisopropoxycyclopentasiloxane, 2,4,6,8,10-pentaethyl-2,4,6,8,10-pentaisopropoxycyclopentasiloxane and 2,4,6,8, 10-pentamethyl-2,4,6,8,10-pentaisopropoxycyclopentasiloxane, Further examples include 2,2,4,4,6,6-hexamethoxycyclotrisiloxane, 2,2,4,4,6,6-hexaethoxycyclotrisiloxane, 2,2,4,4, 6,6-hexa-n-propoxycyclotrisiloxane, 2,2,4,4,6,6-hexaisopropoxycyclotrisiloxane, 2,2,4,4,6,6-hexacyclopropoxycyclotrisiloxane, 2,2,4,4,6,6-hexatert-butoxycyclotrisiloxane, 2,2,4,4,6,6-hexasecbutoxycyclotrisiloxane, 2,2,4,4,6,6-hexaisobutoxycyclotrisiloxane, 2,2,4,4,6,6-hexa-n-butoxycyclotrisiloxane and 2,2,4,4,6,6-hexacyclobutoxycyclotrisiloxane.

Further examples include 2,2,4,4,6,6,8,8-octamethoxycyclotetrasiloxane, 2,2,4,4,6,6,8,8-octaethoxycyclotetrasiloxane, 2,2,4,4,6,6,8,8-octa-n-propoxycyclotetrasiloxane, 2,2,4, 4,6,6,8,8-octaisopropoxycyclotetrasiloxane, 2,2,4,4,6,6,8,8-octacyclopropoxycyclotetrasiloxane, 2,2,4,4,6,6,8,8-octatert-butoxycyclotetrasiloxane, 2,2,4,4,6,6,8,8-octasec-botoxycyclotetrasiloxane, 2,2,4,4,6,6,8,8-octaisobutoxycyclotetrasiloxane, 2,2,4,4,6,6,8,8-octa-n-butoxycyclotetrasiloxane and 2,2,4,4,6,6,8,8-octacyclobutoxycyclotetrasiloxane.

Further examples include 2,2,4,4,6,6,8,8,10,10-decamethoxycyclopentasiloxane, 2,2,4,4,6,6,8,8,10,10-decaethoxycyclopentasiloxane, 2,2,4,4,6,6,8,8,10,10-deca-n-propoxycyclopentasiloxane, 2,2,4,4,6,6,8,8,10,10-decaisopropoxycyclopentasiloxane, 2,2,4,4,6,6,8,8,10,10-decacyclopropoxycyclopentasiloxane, 2,2,4,4,6,6,8,8,10,10-decatert-butoxycyclopentasiloxane, 2,2,4,4,6,6,8,8,10,10-decasec-butoxycyclopentasiloxane, 2,2,4,4,6,6,8,8,10,10-decapentaisobutoxycyclopentasiloxane, 2,2,4,4,6,6,8,8,10, 10-deca-n-butoxycyclopentasiloxane and 2,2,4,4,6,6,8,8,10, 10-decacyclobutoxycyclopentasiloxane.

Further examples include 2,4,6-tris(2-methoxyethyl)-2,4, 6-trimethylcyclotrisiloxane, 2,4,6-tris(2-tert-butoxy-ethyl)-2,4,6-trimethylcyclotrisiloxane, 2,4,6,8-tetrakis(2-methoxyethyl)-2,4,6,8-tetramethylcyclotetrasiloxane, 2,4,6,8-tetrakis (2-tert-butoxyethyl)-2,4,6,8-tetramethylcyclotetrasiloxane, 2,4,6,8,10-pentakis(2-methoxyethyl)-2,4,6,8,10-tentamethyl-cyclotpentasiloxane and 2,4,6,8,10-pentakis(2-tert-butoxyethyl)-2,4,6,8,10-pentamethylcyclotetrasiloxane, Further examples include 2,4,6-tris(4-methoxyphenyl)-2, 4,6-trimethylcyclotrisiloxane, 2,4,6-tris(4-tert-butoxyphenyl)-2,4,6-trimethylcyclotrisiloxane, 2,4,6,8-tetrakis(4-methoxyphenyl)-2,4,6,8-tetramethylcyclotetrasiloxane, 2,4, 6,8-tetrakis(4-tert-butoxyphenyl)-2,4,6,8-tetramethylcyclotetrasiloxane, 2,4,6,8,10-pentakis(4-methoxyphenyl)-2,4,6,8,10-pentamethylcyclopentasiloxane and 2,4,6,8,10-pentakis(4-tert-butoxyphenyl)-2,4,6,8,10-pentamethylcyclopentasiloxane.

Further examples include 2,4,6-tris(methoxymethyl)-2,4, 6-trimethylcyclotrisiloxane, 2,4,6-tris(ethoxymethyl)-2,4,6-trimethylcyclotrisiloxane, 2,4,6-tris(n-propoxy-methyl)-2,4, 6-trimethylcyclotrisiloxane, 2,4,6-tris(iso-propoxymethyl)-2,4,6-trimethylcyclotrisiloxane, 2,4,6-tris(n-butoxymethyl)-2,4,6-trimethylcyclotrisiloxane, 2,4,6-tris(iso-butoxymethyl)-2,4,6-trimethylcyclotrisiloxane and 2,4,6-tris (tert-butoxymethyl)-2,4,6-trimethylcyclotrisiloxane.

Further examples include 2,4,6-tris(methoxymethyl)-2,4, 6-triethylcyclotrisiloxane, 2,4,6-tris(ethoxymethyl)-2,4,6-triethylcyclotrisiloxane, 2,4,6-tris(n-propoxy-methyl)-2,4,6-triethylcyclotrisiloxane, 2,4,6-tris(iso-propoxymethyl)-2,4, 6-triethylcyclotrisiloxane, 2,4,6-tris(n-butoxymethyl)-2,4,6-triethylcyclotrisiloxane, 2,4,6-tris(iso-butoxymethyl)-2,4,6-triethylcyclotrisiloxane and 2,4,6-tris(tert-butoxymethyl)-2, 4,6-triethylcyclotrisiloxane.

Further examples include 2,4,6-tris(methoxymethyl)-2,4, 6-triisopropylcyclotrisiloxane, 2,4,6-tris(ethoxy-methyl)-2, 4,6-triisopropylcyclotrisiloxane, 2,4,6-tris(n-propoxymethyl)-2,4,6-triisopropylcyclotrisiloxane, 2,4,6-tris (isopropoxymethyl)-2,4,6-triisopropylcyclotrisiloxane, 2,4, 6-tris(n-butoxymethyl)-2,4,6-triisopropylcyclotrisiloxane, 2,4,6-tris(iso-butoxymethyl)-2,4,6-triisopropylcyclotrisiloxane and 2,4,6-tris(tert-butoxymethyl)-2,4,6-triisopropylcyclotrisiloxane.

Further examples include 2,4,6-tris(methoxymethyl)-2,4,6-tri-n-propylcyclotrisiloxane, 2,4,6-tris(ethoxy-methyl)-2,4,6-tri-n-propylcyclotrisiloxane, 2,4,6-tris(n-propoxymethyl)-2,4,6-tri-n-propylcyclotrisiloxane, 2,4,6-tris(isopropoxymethyl)-2,4,6-tri-n-propylcyclotrisiloxane, 2,4,6-tris(n-butoxymethyl)-2,4,6-tri-n-propylcyclotrisiloxane, 2,4,6-tris(iso-butoxymethyl)-2,4,6-tri-n-propylcyclotrisiloxane and 2,4,6-tris(tert-butoxymethyl)-2,4,6-tri-n-propylcyclotrisiloxane.

Further examples include 2,4,6-tris(methoxymethyl)-2,4,6-tritert-butylcyclotrisiloxane, 2,4,6-tris(ethoxy-methyl)-2,4,6-tritert-butylcyclotrisiloxane, 2,4,6-tris(n-propoxymethyl)-2,4,6-tritert-butylcyclotrisiloxane, 2,4,6-tris(isopropoxymethyl)-2,4,6-tritert-butylcyclotrisiloxane, 2,4,6-tris(n-butoxymethyl)-2,4,6-tritert-butylcyclotrisiloxane, 2,4,6-tris(iso-butoxymethyl)-2,4,6-tritert-butylcyclotrisiloxane and 2,4,6-tris(tert-butoxymethyl)-2,4,6-tritert-butylcyclotrisiloxane.

Further examples include 2,4,6-tris(methoxymethyl)-2,4,6-tricyclopentylcyclotrisiloxane, 2,4,6-tris(ethoxy-methyl)-2,4,6-tricyclopentylcyclotrisiloxane, 2,4,6-tris(n-propoxymethyl)-2,4,6-tricyclopentylcyclotrisiloxane, 2,4,6-tris(isopropoxymethyl)-2,4,6-tricyclopentylcyclotrisiloxane, 2,4,6-tris(n-butoxymethyl)-2,4,6-tricyclopentylcyclotrisiloxane, 2,4,6-tris(iso-butoxymethyl)-2,4,6-tricyclopentylcyclotrisiloxane and 2,4,6-tris(tert-butoxymethyl)-2,4,6-tricyclopentylcyclotrisiloxane.

Further examples include 2,4,6-tris(methoxymethyl)-2,4,6-tricyclohexylcyclotrisiloxane, 2,4,6-tris(ethoxy-methyl)-2,4,6-tricyclohexylcyclotrisiloxane, 2,4,6-tris(n-propoxymethyl)-2,4,6-tricyclohexylcyclotrisiloxane, 2,4,6-tris(isopropoxymethyl)-2,4,6-tricyclohexylcyclotrisiloxane, 2,4,6-tris(n-butoxymethyl)-2,4,6-tricyclohexylcyclotrisiloxane, 2,4,6-tris(iso-butoxymethyl)-2,4,6-tricyclohexylcyclotrisiloxane and 2,4,6-tris(tert-butoxymethyl)-2,4,6-tricyclohexylcyclotrisiloxane.

Further examples include 2,4,6-tris(methoxyethyl)-2,4,6-trimethylcyclotrisiloxane, 2,4,6-tris(ethoxyethyl)-2,4,6-trimethylcyclotrisiloxane, 2,4,6-tris(n-propoxy-ethyl)-2,4,6-trimethylcyclotrisiloxane, 2,4,6-tris(iso-propoxyethyl)-2,4,6-trimethylcyclotrisiloxane, 2,4,6-tris(n-butoxyethyl)-2,4,6-trimethylcyclotrisiloxane, 2,4,6-tris(iso-butoxyethyl)-2,4,6-trimethylcyclotrisiloxane and 2,4,6-tris(tert-butoxyethyl)-2,4,6-trimethylcyclotrisiloxane.

Further examples include 2,4,6-tris(methoxyethyl)-2,4,6-triethylcyclotrisiloxane, 2,4,6-tris(ethoxyethyl)-2,4,6-triethylcyclotrisiloxane, 2,4,6-tris(n-propoxyethyl)-2,4,6-triethylcyclotrisiloxane, 2,4,6-tris(isopropoxyethyl)-2,4,6-triethylcyclotrisiloxane, 2,4,6-tris(n-butoxyethyl)-2,4,6-triethylcyclotrisiloxane, 2,4,6-tris-(iso-butoxyethyl)-2,4,6-triethylcyclotrisiloxane and 2,4,6-tris(tert-butoxyethyl)-2,4,6-triethylcyclotrisiloxane.

Further examples include 2,4,6-tris(methoxyethyl)-2,4,6-triisopropylcyclotrisiloxane, 2,4,6-tris(ethoxy-ethyl)-2,4,6-triisopropylcyclotrisiloxane, 2,4,6-tris(n-propoxyethyl)-2,4,6-triisopropylcyclotrisiloxane, 2,4,6-tris(isopropoxyethyl)-2,4,6-triisopropylcyclotrisiloxane, 2,4,6-tris(n-butoxyethyl)-2,4,6-triisopropylcyclotrisiloxane, 2,4,6-tris(iso-butoxyethyl)-2,4,6-triisopropylcyclotrisiloxane and 2,4,6-tris(tert-butoxyethyl)-2,4,6-triisopropylcyclotrisiloxane.

Further examples include 2,4,6-tris(methoxyethyl)-2,4,6-tri-n-propylcyclotrisiloxane, 2,4,6-tris(ethoxy-ethyl)-2,4,6-tri-n-propylcyclotrisiloxane, 2,4,6-tris(n-propoxyethyl)-2,4,6-tri-n-propylcyclotrisiloxane, 2,4,6-tris(isopropoxyethyl)-2,4,6-tri-n-propylcyclotrisiloxane, 2,4,6-tris(n-butoxyethyl)-2,4,6-tri-n-propylcyclotrisiloxane, 2,4,6-tris(iso-butoxyethyl)-2,4,6-tri-n-propylcyclotrisiloxane and 2,4,6-tris(tert-butoxyethyl)-2,4,6-tri-n-propylcyclotrisiloxane.

Further examples include 2,4,6-tris(methoxyethyl)-2,4,6-tritert-butylcyclotrisiloxane, 2,4,6-tris(ethoxy-ethyl)-2,4,6-tritert-butylcyclotrisiloxane, 2,4,6-tris(n-propoxyethyl)-2,4,6-tritert-butylcyclotrisiloxane, 2,4,6-tris(isopropoxyethyl)-2,4,6-tritert-butylcyclotrisiloxane, 2,4,6-tris(n-butoxyethyl)-2,4,6-tritert-butylcyclotrisiloxane, 2,4,6-tris(iso-butoxyethyl)-2,4,6-tritert-butylcyclotrisiloxane and 2,4,6-tris(tert-butoxyethyl)-2,4,6-tritert-butylcyclotrisiloxane.

Further examples include 2,4,6-tris(methoxyethyl)-2,4,6-tricyclopentylcyclotrisiloxane, 2,4,6-tris(ethoxy-ethyl)-2,4,6-tricyclopentylcyclotrisiloxane, 2,4,6-tris(n-propoxyethyl)-2,4,6-tricyclopentylcyclotrisiloxane, 2,4,6-tris(isopropoxyethyl)-2,4,6-tricyclopentylcyclotrisiloxane, 2,4,6-tris(n-butoxyethyl)-2,4,6-tricyclopentylcyclotrisiloxane, 2,4,6-tris(iso-butoxyethyl)-2,4,6-tricyclopentylcyclotrisiloxane and 2,4,6-tris(tert-butoxyethyl)-2,4,6-tricyclopentylcyclotrisiloxane.

Further examples include 2,4,6-tris(methoxyethyl)-2,4,6-tricyclohexylcyclotrisiloxane, 2,4,6-tris(ethoxy-ethyl)-2,4,6-tricyclohexylcyclotrisiloxane, 2,4,6-tris(n-propoxyethyl)-2,4,6-tricyclohexylcyclotrisiloxane, 2,4,6-tris(isopropoxyethyl)-2,4,6-tricyclohexylcyclotrisiloxane, 2,4,6-tris(n-butoxyethyl)-2,4,6-tricyclohexylcyclotrisiloxane, 2,4,6-tris(iso-butoxyethyl)-2,4,6-tricyclohexylcyclotrisiloxane and 2,4,6-tris(tert-butoxyethyl)-2,4,6-tricyclohexylcyclotrisiloxane.

Further examples include 2,4,6-tris(methoxypropyl)-2,4,6-trimethylcyclotrisiloxane, 2,4,6-tris(methoxypropyl)-2,4,6-triethylcyclotrisiloxane, 2,4,6-tris(methoxypropyl)-2,4,6-triisopropylcyclotrisiloxane, 2,4,6-tris(methoxybutyl)-2,4,6-trimethylcyclotrisiloxane, 2,4,6-tris-(methoxypentyl)-2,4,6-trimethylcyclotrisiloxane and 2,4,6-tris(methoxyhexyl)-2,4,6-trimethylcyclotrisiloxane.

Further examples include 2,4,6,8-tetrakis-(methoxymethyl)-2,4,6,8-tetramethylcyclotetrasiloxane, 2,4,6,8-tetrakis(ethoxymethyl)-2,4,6,8-tetramethylcyclotetrasiloxane, 2,4,6,8-tetrakis(n-propoxymethyl)-2,4,6,8-tetramethylcyclotetrasiloxane, 2,4,6,8-tetrakis(isopropoxymethyl)-2,4,6,8-tetramethylcyclotetrasiloxane, 2,4,6,8-tetrakis(n-butoxymethyl)-2,4,6,8-tetramethylcyclotetrasiloxane, 2,4,6,8-tetrakis(isobutoxymethyl)-2,4,6,8-tetramethylcyclotetrasiloxane and 2,4,6,8-tetrakis(tert-butoxymethyl)-2,4,6,8-tetramethylcyclotetrasiloxane.

Further examples include 2,4,6,8-tetrakis-(methoxymethyl)-2,4,6,8-tetraethylcyclotetrasiloxane, 2,4,6,8-tetrakis(ethoxymethyl)-2,4,6,8-tetraethylcyclotetrasiloxane, 2,4,6,8-tetrakis(n-propoxymethyl)-2,4,6,8-tetraethylcyclotetrasiloxane, 2,4,6,8-tetrakis(isopropoxymethyl)-2,4,6,8-tetraethylcyclotetrasiloxane, 2,4,6,8-tetrakis(n-butoxymethyl)-2,4,6,8-tetraethylcyclotetrasiloxane, 2,4,6,8-tetrakis(isobutoxymethyl)-2,4,6,8-tetraethylcyclotetrasiloxane and 2,4,6,8-tetrakis(tert-butoxymethyl)-2,4,6,8-tetraethylcyclotetrasiloxane.

Further examples include 2,4,6,8-tetrakis-(methoxymethyl)-2,4,6,8-tetra-n-propylcyclotetrasiloxane, 2,4,6,8-tetrakis(ethoxymethyl)-2,4,6,8-tetra-n-propylcyclotetrasiloxane, 2,4,6,8-tetrakis(n-propoxymethyl)-2,4,6,8-tetra-n-propylcyclotetrasiloxane, 2,4,6,8-tetrakis(isopropoxymethyl)-2,4,6,8-tetra-n-propylcyclotetrasiloxane, 2,4,6,8-tetrakis(n-butoxymethyl)-2,4,6,8-tetra-n-propylcyclotetrasiloxane, 2,4,6,8-tetrakis(isobutoxymethyl)-2,4,6,8-tetra-n-propylcyclotetrasiloxane and 2,4,6,8-tetrakis(tert-butoxymethyl)-2,4,6,8-tetra-n-propylcyclotetrasiloxane.

Further examples include 2,4,6,8-tetrakis(methoxymethyl)-2,4,6,8-tetraisopropylcyclotetrasiloxane, 2,4,6,8-tetrakis(ethoxymethyl)-2,4,6,8-tetraisopropylcyclotetrasiloxane, 2,4,6,8-tetrakis(n-propoxymethyl)-2,4,6,8-tetraisopropylcyclotetrasiloxane, 2,4,6,8-tetrakis(isopropoxymethyl)-2,4,6,8-tetraisopropylcyclotetrasiloxane, 2,4,6,8-tetrakis(n-butoxymethyl)-2,4,6,8-tetraisopropylcyclotetrasiloxane, 2,4,6,8-tetrakis(isobutoxymethyl)-2,4,6,8-tetraisopropylcyclotetrasiloxane and 2,4,6,8-tetrakis(tert-butoxymethyl)-2,4,6,8-tetraisopropylcyclotetrasiloxane.

Further examples include 2,4,6,8-tetrakis-(methoxymethyl)-2,4,6,8-tetratert-butylcyclotetrasiloxane, 2,4,6,8-tetrakis(ethoxymethyl)-2,4,6,8-tetratert-butyl-cyclotetrasiloxane, 2,4,6,8-tetrakis(n-propoxymethyl)-2,4,6,8-tetratert-butylcyclotetrasiloxane, 2,4,6,8-tetrakis(isopropoxymethyl)-2,4,6,8-tetratert-butylcyclotetrasiloxane, 2,4,6,8-tetrakis(n-butoxymethyl)-2,4,6,8-tetratert-butylcyclotetrasiloxane, 2,4,6,8-tetrakis(isobutoxymethyl)-2,4,6,8-tetratert-butylcyclotetrasiloxane and 2,4,6,8-tetrakis(tert-butoxymethyl)-2,4,6,8-tetratert-butylcyclotetrasiloxane.

Further examples include 2,4,6,8-tetrakis-(methoxymethyl)-2,4,6,8-tetracyclopentylcyclotetrasiloxane, 2,4,6,8-tetrakis(ethoxymethyl)-2,4,6,8-tetracyclopentylcyclotetrasiloxane, 2,4,6,8-tetrakis(n-propoxymethyl)-2,4,6,8-tetracyclopentylcyclotetrasiloxane, 2,4,6,8-tetrakis(isopropoxymethyl)-2,4,6,8-tetracyclopentylcyclotetrasiloxane, 2,4,6,8-tetrakis(n-butoxymethyl)-2,4,6,8-tetracyclopentylcyclotetrasiloxane, 2,4,6,8-tetrakis(isobutoxymethyl)-2,4,6,8-tetracyclopentylcyclotetrasiloxane and 2,4,6,8-tetrakis(tert-butoxymethyl)-2,4,6,8-tetracyclopentylcyclotetrasiloxane.

Further examples include 2,4,6,8-tetrakis-(methoxymethyl)-2,4,6,8-tetracyclohexylcyclotetrasiloxane, 2,4,6,8-tetrakis(ethoxymethyl)-2,4,6,8-tetracyclohexylcyclotetrasiloxane, 2,4,6,8-tetrakis(n-propoxymethyl)-2,4,6,8-tetracyclohexylcyclotetrasiloxane, 2,4,6,8-tetrakis(isopropoxymethyl)-2,4,6,8-tetracyclohexylcyclotetrasiloxane, 2,4,6,8-tetrakis(n-butoxymethyl)-2,4,6,8-tetracyclohexylcyclotetrasiloxane, 2,4,6,8-tetrakis(iso-butoxymethyl)-2,4,6,8-tetracyclohexylcyclotetrasiloxane and 2,4,6,8-tetrakis(tert-butoxymethyl)-2,4,6,8-tetracyclohexylcyclotetrasiloxane.

Further examples include 2,4,6,8-tetrakis-(methoxyethyl)-2,4,6,8-tetramethylcyclotetrasiloxane, 2,4,6,8-tetrakis(ethoxyethyl)-2,4,6,8-tetramethylcyclotetrasiloxane, 2,4,6,8-tetrakis(n-propoxyethyl)-2,4,6,8-tetramethylcyclotetrasiloxane, 2,4,6,8-tetrakis(isopropoxyethyl)-2,4,6,8-tetramethylcyclotetrasiloxane, 2,4,6,8-tetrakis(n-butoxyethyl)-2,4,6,8-tetramethylcyclotetrasiloxane, 2,4,6,8-tetrakis(isobutoxyethyl)-2,4,6,8-tetramethylcyclotetrasiloxane and 2,4,6,8-tetrakis(tert-butoxyethyl)-2,4,6,8-tetramethylcyclotetrasiloxane.

Further examples include 2,4,6,8-tetrakis-(methoxyethyl)-2,4,6,8-tetraethylcyclotetrasiloxane, 2,4,6,8-tetrakis(ethoxyethyl)-2,4,6,8-tetraethylcyclotetrasiloxane, 2,4,6,8-tetrakis(n-propoxyethyl)-2,4,6,8-tetraethylcyclotetrasiloxane, 2,4,6,8-tetrakis(isopropoxyethyl)-2,4,6,8-tetraethylcyclotetrasiloxane, 2,4,6,8-tetrakis(n-butoxyethyl)-2,4,6,8-tetraethylcyclotetrasiloxane, 2,4,6,8-tetrakis(isobutoxyethyl)-2,4,6,8-tetraethylcyclotetrasiloxane and 2,4,6,8-tetrakis(tert-butoxyethyl)-2,4,6,8-tetraethylcyclotetrasiloxane.

Further examples include 2,4,6,8-tetrakis-(methoxyethyl)-2,4,6,8-tetra-n-propylcyclotetrasiloxane, 2,4,6,8-tetrakis(ethoxyethyl)-2,4,6,8-tetra-n-propylcyclotetrasiloxane, 2,4,6,8-tetrakis(n-propoxyethyl)-2,4,6,8-tetra-n-propylcyclotetrasiloxane, 2,4,6,8-tetrakis(isopropoxyethyl)-2,4,6,8-tetra-n-propylcyclotetrasiloxane, 2,4,6,8-tetrakis(n-butoxyethyl)-2,4,6,8-tetra-n-propylcyclotetrasiloxane, 2,4,6,8-tetrakis(isobutoxyethyl)-2,4,6,8-tetra-n-propylcyclotetrasiloxane and 2,4,6,8-tetrakis(tert-butoxyethyl)-2,4,6,8-tetra-n-propylcyclotetrasiloxane.

Further examples include 2,4,6,8-tetrakis-(methoxyethyl)-2,4,6,8-tetraisopropylcyclotetrasiloxane, 2,4,6,8-tetrakis(ethoxyethyl)-2,4,6,8-tetraisopropylcyclotetrasiloxane, 2,4,6,8-tetrakis(n-propoxyethyl)-2,4,6,8-tetraisopropylcyclotetrasiloxane, 2,4,6,8-tetrakis(isopropoxyethyl)-2,4,6,8-tetraisopropylcyclotetrasiloxane, 2,4,6,8-tetrakis(n-butoxyethyl)-2,4,6,8-tetraisopropylcyclotetrasiloxane, 2,4,6,8-tetrakis(isobutoxyethyl)-2,4,6,8-tetraisopropylcyclotetrasiloxane and 2,4,6,8-tetrakis(tert-butoxyethyl)-2,4,6,8-tetraisopropylcyclotetrasiloxane.

Further examples include 2,4,6,8-tetrakis-(methoxyethyl)-2,4,6,8-tetratert-butylcyclotetrasiloxane, 2,4,6,8-tetrakis(ethoxyethyl)-2,4,6,8-tetratert-butyl-cyclotetrasiloxane, 2,4,6,8-tetrakis(n-propoxyethyl)-2,4,6,8-tetratert-butylcyclotetrasiloxane, 2,4,6,8-tetrakis(isopropoxyethyl)-2,4,6,8-tetratert-butylcyclotetrasiloxane, 2,4,6,8-tetrakis(n-butoxyethyl)-2,4,6,8-tetratert-butylcyclotetrasiloxane, 2,4,6,8-tetrakis(isobutoxyethyl)-2,4,6,8-tetratert-butylcyclotetrasiloxane and 2,4,6,8-tetrakis(tert-butoxyethyl)-2,4,6,8-tetratert-butylcyclotetrasiloxane.

Further examples include 2,4,6,8-tetrakis-(methoxyethyl)-2,4,6,8-tetracyclopentylcyclotetrasiloxane, 2,4,6,8-tetrakis(ethoxyethyl)-2,4,6,8-tetracyclopentylcyclotetrasiloxane, 2,4,6,8-tetrakis(n-propoxyethyl)-2,4,6,8-tetracyclopentylcyclotetrasiloxane, 2,4,6,8-tetrakis(isopropoxyethyl)-2,4,6,8-tetracyclopentylcyclotetrasiloxane, 2,4,6,8-tetrakis(n-butoxyethyl)-2,4,6,8-tetracyclopentylcyclotetrasiloxane, 2,4,6,8-tetrakis(isobutoxyethyl)-2,4,6,8-tetracyclopentylcyclotetrasiloxane and 2,4,6,8-tetrakis(tert-butoxyethyl)-2,4,6,8-tetracyclopentylcyclotetrasiloxane.

Further examples include 2,4,6,8-tetrakis-(methoxyethyl)-2,4,6,8-tetracyclohexylcyclotetrasiloxane, 2,4,6,8-tetrakis(ethoxyethyl)-2,4,6,8-tetracyclohexylcyclotetrasiloxane, 2,4,6,8-tetrakis(n-propoxyethyl)-2,4,6,8-tetracyclohexylcyclotetrasiloxane, 2,4,6,8-tetrakis(isopropoxyethyl)-2,4,6,8-tetracyclohexylcyclotetrasiloxane, 2,4,6,8-tetrakis(n-butoxyethyl)-2,4,6,8-tetracyclohexylcyclotetrasiloxane, 2,4,6,8-tetrakis(iso-butoxyethyl)-2,4,6,8-tetracyclohexylcyclotetrasiloxane and 2,4,6,8-tetrakis(tert-butoxyethyl)-2,4,6,8-tetracyclohexylcyclotetrasiloxane.

Further examples include 2,4,6,8-tetrakis-(methoxypropyl)-2,4,6,8-tetramethylcyclotrisiloxane, 2,4,6,8-tetrakis(methoxypropyl)-2,4,6,8-tetraethylcyclo-trisiloxane, 2,4,6,8-tetrakis(methoxypropyl)-2,4,6,8-tetraisopropylcyclotrisiloxane, 2,4,6,8-tetrakis(methoxybutyl)-2,4,6,8-tetramethylcyclotrisiloxane, 2,4,6,8-tetrakis(methoxypentyl)-2,4,6,8-tetramethylcyclotrisiloxane and 2,4,6,8-tetrakis(methoxyhexyl)-2,4,6,8-tetramethylcyclotrisiloxane.

Further examples include 2,4,6,8,10-pentakis-(methoxymethyl)-2,4,6,8,10-pentamethylcyclopentasiloxane, 2,4,6,8,10-pentakis(methoxymethyl)-2,4,6,8,10-pentaethylcyclopentasiloxane and 2,4,6,8,10-pentakis(methoxymethyl)-2,4,6,8,10-pentaisopropylcyclopentasiloxane.

Further examples include 2,4,6,8,10-pentakis-(methoxyethyl)-2,4,6,8,10-pentamethylcyclopentasiloxane, 2,4,6,8,10-pentakis(methoxyethyl)-2,4,6,8,10-pentaethylcyclopentasiloxane and 2,4,6,8,10-pentakis(methoxyethyl)-2,4,6,8,10-pentaisopropylcyclopentasiloxane.

Further examples include 2,4,6-tritert-butyl-2,4,6-tris(dimethylamino)cyclotrisiloxane, 2,4,6-tritert-butyl-2,4,6-tris(diethylamino)cyclotrisiloxane, 2,4,6,8-tetra-tert-butyl-2,4,6,8-tetrakis(dimethylamino)cyclotetrasiloxane, 2,4,6,8-tetratert-butyl-2,4,6,8-tetrakis-(diethylamino)cyclotetrasiloxane, 2,4,6,8,10-pentatert-butyl-2,4,6,8,10-pentakis(dimethylamino)cyclopentasiloxane and 2,4,6,8,10-pentatert-butyl-2,4,6,8,10-pentakis(diethylamino)cyclopentasiloxane.

Further examples include 2,4,6-triisopropyl-2,4,6-tris(dimethylamino)cyclotrisiloxane, 2,4,6-triisopropyl-2,4,6-tris(diethylamino)cyclotrisiloxane, 2,4,6,8-tetraisopropyl-2,4,6,8-tetrakis(dimethylamino)cyclotetrasiloxane, 2,4,6,8-tetraisopropyl-2,4,6,8-tetrakis(diethylamino)-cyclotetrasiloxane, 2,4,6,8,10-pentaisopropyl-2,4,6,8,10-pentakis(dimethylamino)cyclopentasiloxane and 2,4,6,8,10-pentaisopropyl-2,4,6,8,10-pentakis(diethylamino)cyclopentasiloxane.

Further examples include 2,4,6-trimethyl-2,4,6-tris(dimethylamino)cyclotrisiloxane, 2,4,6-trimethyl-2,4,6-tris(diethylamino)cyclotrisiloxane, 2,4,6,8-tetramethyl-2,4,6,8-tetrakis(dimethylamino)cyclotetrasiloxane, 2,4,6,8-tetramethyl-2,4,6,8-tetrakis(diethylamino)cyclotetrasiloxane, 2,4,6,8,10-pentamethyl-2,4,6,8,10-pentakis-(dimethylamino)cyclopentasiloxane and 2,4,6,8,10-pentamethyl-2,4,6,8,10-pentakis(diethylamino)cyclopentasiloxane.

Further examples include 2,4,6-tris(4-dimethylaminophenyl)-2,4,6-trimethylcyclotrisiloxane, 2,4,6-tris(4-diethylaminophenyl)-2,4,6-trimethylcyclotrisiloxane, 2,4,6,8-tetrakis(4-dimethylaminophenyl)-2,4,6,8-tetramethylcyclotetrasiloxane, 2,4,6,8-tetrakis(4-diethylaminophenyl)-2,4,6,8-tetramethylcyclotetrasiloxane, 2,4,6,8,10-pentakis(4-dimethylaminophenyl)-2,4,6,8,10-pentamethylcyclopentasiloxane and 2,4,6,8,10-pentakis(4-diethylaminophenyl)-2,4,6,8,10-pentamethylcyclopentasiloxane.

Further examples include 2,4,6-tritert-butyl-2,4,6-tris(dimethylboro)cyclotrisiloxane, 2,4,6-tritert-butyl-2,4,6-tris(diethylboro)cyclotrisiloxane, 2,4,6,8-tetratertbutyl-2,4,6,8-tetrakis(dimethylboro)cyclotetrasiloxane, 2,4,6,8-tetratert-butyl-2,4,6,8-tetrakis(diethylboro)-cyclotetrasiloxane, 2,4,6,8,10-pentatert-butyl-2,4,6,8,10-pentakis(dimethylboro)cyclopentasiloxane and 2,4,6,8,10-pentatert-butyl-2,4,6,8,10-pentakis(diethylboro)cyclopentasiloxane.

Further examples include 2,4,6-triisopropyl-2,4,6-tris(dimethylboro)cyclotrisiloxane, 2,4,6-triisopropyl-2,4,6-tris(diethylboro)cyclotrisiloxane, 2,4,6,8-tetraisopropyl-2,4,6,8-tetrakis(dimethylboro)cyclotetrasiloxane, 2,4,6,8-tetraisopropyl-2,4,6,8-tetrakis(diethylboro)-cyclotetrasiloxane, 2,4,6,8,10-pentaisopropyl-2,4,6,8,10-pentakis(dimethylboro)cyclopentasiloxane and 2,4,6,8,10-pentaisopropyl-2,4,6,8,10-pentakis(diethylboro)cyclopentasiloxane.

Further examples include 2,4,6-trimethyl-2,4,6-tris(dimethylboro)cyclotrisiloxane, 2,4,6-trimethyl-2,4,6-tris(diethylboro)cyclotrisiloxane, 2,4,6,8-tetramethyl-2,4,6,8-tetrakis(dimethylboro)cyclotetrasiloxane, 2,4,6,8-tetramethyl-2,4,6,8-tetrakis(diethylboro)cyclotetrasiloxane, 2,4,6,8,10-pentamethyl-2,4,6,8,10-pentakis(dimethylboro)-cyclopentasiloxane and 2,4,6,8,10-pentamethyl-2,4,6,8,10-pentakis(diethylboro)cyclopentasiloxane.

Further examples include 2,4,6-tris(4-dimethyl-borophenyl)-2,4,6-trimethylcyclotrisiloxane, 2,4,6-tris(4-diethyl-borophenyl)-2,4,6-trimethylcyclotrisiloxane, 2,4,6,8-tetrakis(4-dimethylborophenyl)-2,4,6,8-tetramethylcyclotetrasiloxane, 2,4,6,8-tetrakis(4-diethylborophenyl)-2,4,6,8-tetramethyl-cyclotetrasiloxane, 2,4,6,8,10-pentakis(4-dimethylborophenyl)-2,4,6,8,10-pentamethylcyclopentasiloxane and 2,4,6,8,10-pentakis(4-diethylborophenyl)-2,4,6,8,10-pentamethylcyclopentasiloxane.

The material for forming Si-containing film of the present invention contains the cyclic siloxane compound represented by the general formula (1). When it is used as an insulting film material, it is preferable that the amount of impurities other than silicon, carbon, oxygen, hydrogen, nitrogen and boron is less than 10 ppb, and a water content is less than 50 ppm.

The production method of the cyclic siloxane compound represented by the general formula (1) is not particularly limited, but the method of producing the cyclic siloxane compound having the structure of the general formula (2) can use, for example, a method of hydrolyzing an oxygen-containing silane compound represented by the following general formula (8)

[Chem. 9]

(8)

(In the formula, $R^1$ and $R^8$ are the same as defined above.), in the presence or absence of an acid or a base, and a method of producing by reacting a cyclic siloxane represented by the following general formula (9)

[Chem. 10]

(9)

(In the formula, $R^1$, n and x are the same as defined above), and alcohols in the presence of Pd, Ni or Rh catalyst.

The method of producing the cyclic siloxane compound having the structure of the general formula (3) can use, for example, a method of hydrolyzing an oxygen-containing silane compound represented by the following general formula (10)

[Chem. 11]

(10)

(In the formula, $R^1$, $R^2$, $R^3$, $R^9$ and p are the same as defined above. s is 1 or 2, t is 0 or 1, and s+t is 1 to 2.), obtained by reacting the corresponding Grignard reagent or organic lithium compound, and an organic silane compound, in the presence or absence of an acid or a base, and a method of producing by reacting the cyclic siloxane represented by the general formula (9) and an alkyne compound having $R^2O$ group in the presence of Pt catalyst.

The method of producing the cyclic siloxane having the structure of the general formula (4) can use, for example, a method of hydrolyzing a nitrogen- or oxygen-containing silane compound represented by the following general formula (11)

[Chem. 12]

(11)

(In the formula, $R^1$, $R^4$ and $R^{10}$ are the same as defined above. u is 1 or 2, v is 0 or 1, and u+v is 1 to 2.),
in the presence or absence of an acid or a base.

The method of producing the cyclic siloxane compound having the structure of the general formula (5) can use, for example, a method of hydrolyzing a nitrogen- or oxygen-containing silane compound represented by the following general formula (12)

[Chem. 13]

(12)

(In the formula, $R^1$, $R^4$, $R^5$, $R^{11}$ and q are the same as defined above. y is 1 or 2, z is 0 or 1, and y+z is 1 to 2.),
in the presence or absence of an acid or a base.

The method of producing the cyclic siloxane having the structure of the general formula (6) can use, for example, a method of hydrolyzing a boron- or oxygen-containing silane compound represented by the following general formula (13)

[Chem. 14]

(13)

(In the formula, $R^1$, $R^6$ and $R^{12}$ are the same as defined above. a is 1 or 2, b is 0 or 1, and a+b is 1 to 2.),
in the presence or absence of an acid or a base.

The method of producing the cyclic siloxane having the structure of the general formula (7) can use, for example, a method of hydrolyzing a boron- or oxygen-containing silane compound represented by the following general formula (14)

[Chem. 15]

(14)

(In the formula, $R^1$, $R^6$, $R^7$, $R^{13}$ and r are the same as defined above. c is 1 or 2, d is 0 or 1, and c+d is 1 to 2.),
in the presence or absence of an acid or a base.

In conducting the reaction, inorganic acids such as hydrochloric acid, nitric acid and sulfuric acid, and organic acids such as toluenesulfonic acid can be used as an acid to be present. Further, in conducting the reaction, sodium hydroxide, potassium hydroxide, sodium methoxide, potassium methoxide, sodium ethoxide, potassium ethoxide, sodium tertiary butoxide, potassium tertiary butoxide or the like can be used as a base to be present.

The Pd, Ni or Rh catalyst that can be used in reacting the cyclic siloxane compound of the general formula (9) and alcohols includes Pd(0), Ni(0) or Rh(0) catalyst supported on a high surface area activated carbon, and a heterogeneous or homogeneous catalyst represented by the following general formula (15)

[Chem. 16]

$$MX_eL_f \qquad (15)$$

(In the formula, M represents Pd, Ni or Rh, X represents fluorine, chlorine, bromine and iodine, and L represents an electron donating compound. e and f are a number of 0 or more, and e+f is a number satisfying the valency of M and coordination number).

A phosphine compound, an amine compound and the like can be used as the electron donating compound represented by L in the general formula (15). Specifically, a phosphine compound represented by the following general formula (16) or general formula (17)

[Chem. 17]

$$PR^{14}_3 \qquad (16)$$

(In the formula, $R^{14}$ is the same as defined above. $R^{14}$s may be the same or different.)

[Chem. 18]

(17)

(In the formula, $R^{15}$ is the same as defined above. $R^{15}$s may be the same or different.),
or an amine compound represented by the following general formula (18) or (19)

[Chem. 19]

$$NR^{16}_3 \qquad (18)$$

(In the formula, $R^{16}$ is the same as defined above. $R^{16}$s may be the same or different.)

[Chem. 20]

(19)

(In the formula, $R^{17}$ is the same as defined above. $R^{17}$s may be the same or different.),
can be used.

The reaction solvent that can be used in producing the cyclic siloxane compound represented by the general formula (1) is not particularly limited so far as it is used in the art of this field. Examples of the solvent that can be used include saturated hydrocarbons such as n-pentane, i-pentane, n-hexane, cyclohexane, n-heptane and n-decane; unsaturated hydrocarbons such as toluene, xylene and decene-1; ethers such as diethyl ether, dipropyl ether, tert-butyl methyl ether, dibutyl ether, cyclopentyl methyl ether and tetrahydrofuran; and alcohols such as methanol, ethanol, isopropanol, n-butanol, tert-butanol and 2-ethylhexanol. Mixed solvents of those can be used. Especially, when ethers or alcohols are used, there is the case that the cyclic siloxane compound represented by the general formula (1) having a specific molecular weight can be produced in high yield.

The reaction temperature in producing the cyclic siloxane compound represented by the general formula (1) is in a range of from −100 to 200° C. which is a temperature generally used industrially, and preferably in a range of from −85 to 150° C. Pressure condition of the reaction can be under pressure, at normal pressures or under reduced pressure.

Purification method of the cyclic siloxane compound represented by the general formula (1) produced can use a purification method such as distillation at normal pressures or under reduced pressure, or column separation using silica, alumina or polymer gel, in order to reduce a water content which is useful to use as an insulating film material to less than 50 ppm, and the amount of impurities other than silicon, carbon, oxygen and hydrogen, such as the amount of metal impurities, to less than 10 ppb. In this case, those methods may be combined according to need.

Where a water content, and the amount of impurities of elements other than silicon, carbon, oxygen and hydrogen, especially residue of metal impurities, in the cyclic siloxane compound represented by the general formula (1) finally obtained are high, such a compound is not suitable as an insulating film material.

In the production, other conditions preferably follow the methods in the fields of organic synthesis and organic metal compound synthesis. Specifically, it is preferable that the production is conducted in a water-removed and deoxidized nitrogen or argon atmosphere, and water-removal operation is previously applied to a solvent used and a column filler for purification. Further, it is preferable that impurities such as metal residues and particles are removed.

The cyclic siloxane compound represented by the general formula (1) of the present invention is used as a material for forming Si-containing film, and an Si-containing film can be produced using the same as a raw material. In this case, the film forming method is not limited, but it is preferable to conduct the method by CVD, and it is especially preferable to conduct by PECVD.

The kind of PECVD and equipment used in this case are not particularly limited. For example, PECVD uses the method generally used in this technical field such as semiconductor production field and liquid crystal display production field.

In the PECVD equipment, the material for forming Si-containing film of the present invention is vaporized with a vaporizer and introduced into a film formation chamber, a voltage is applied to an electrode in the film formation chamber by a high frequency power source to generate plasma, thereby forming a plasma CVD thin film on a silicon substrate or the like in the film formation chamber. In this case, a gas such as argon or helium and an oxidizing agent such as oxygen or nitrous oxide may be introduced for the purpose of generating plasma. Further, simultaneous introduction of an organic peroxide or an epoxy compound for the purpose of forming pores in a thin film is also included in the scope of the present invention. When a film is formed using the material for forming Si-containing film of the present invention by a PECVD equipment, a thin film suitable as a low dielectric constant material (Low-k material) for semiconductor device can be formed.

The plasma generation method of PECVD equipment is not particularly limited, and inductively coupled plasma, capacitively coupled plasma, ECR plasma, microwave plasma and the like that are used in the art can be used. Inductively coupled plasma and capacitively coupled plasma are preferable. As a plasma generation source, various types such as parallel plate type and antenna type can be used, and as an inert gas supplied to a chamber of the PECVD equipment, helium, argon, krypton, neon, xenon and the like that are used in this technical field can be used.

Figure 1:
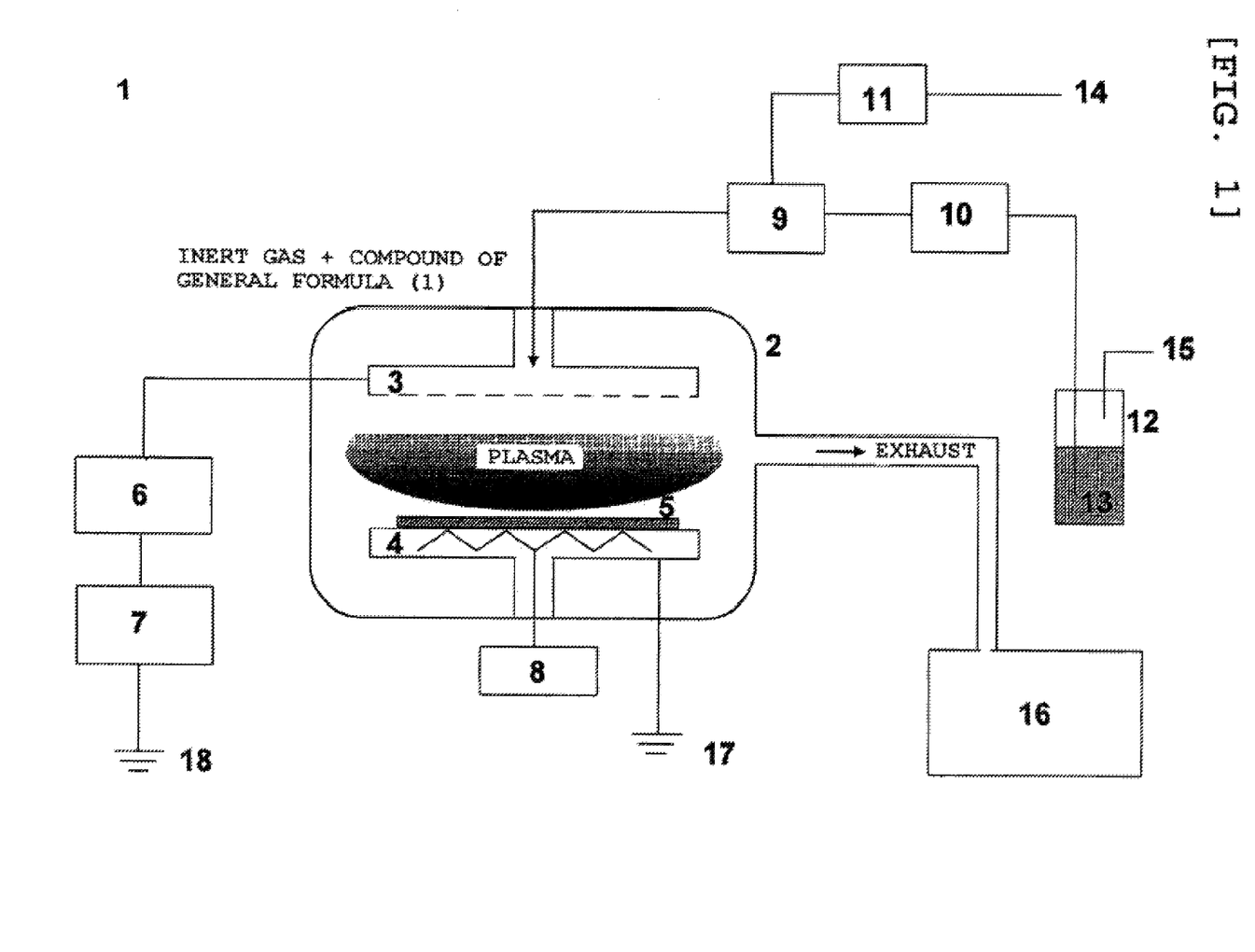
FIG. 1 is a view showing a parallel plate capacitively coupled PECVD equipment.

As one example of the PECVD equipment, a parallel plate capacitively coupled PECVD equipment is shown in FIG. 1. A parallel plate capacitively coupled PECVD equipment 1 shown in FIG. 1 comprises a shower head upper electrode and a lower electrode capable of controlling temperature of a substrate in a PECVD equipment chamber, a vaporization equipment which vaporizes the general formula (1) and supplies to the chamber, a plasma generation equipment comprising a high frequency power source and a matching circuit, and an exhaust system comprising a vacuum pump.

Specifically, the PECVD equipment 1 comprises a PECVD chamber 2, an upper electrode 3 having a shower head for uniformly supplying the compound of the general formula (1) in the chamber, a lower electrode 4 having a temperature control device 8 for setting a thin film forming substrate 5 such as an Si substrate, vaporization equipment 9 to 15 for vaporizing the compound of the general formula (1), a matching circuit 6 and a RF power source 7, that are a plasma generation source, and an exhaust equipment 16 for exhausting an unreacted product and a by-product in the chamber. 17 and 18 are earth ground.

The matching circuit 6 and RF power source 7, that are a plasma generation source are connected to the upper electrode 3, and plasma is generated by discharging. The standard of the RF power source 7 is not particularly limited, but the RF power source generally used in this technical field, having electric power of from 1 W to 2,000 W, and preferably from 10 W to 1,000 W, and a frequency of from 50 kHz to 2.5 GHz, preferably from 100 kHz to 100 MHz, and particularly preferably from 200 kHz to 50 MHz, can be used.

Control of substrate temperature is not particularly limited, but the temperature is in a range of from −90 to 1,000° C., and preferably from 0° C. to 500° C.

The vaporization equipment comprises a container 12 filled with the compound 13 of the general formula (1) which is liquid at ordinary temperature and normal pressures and equipped with a dip piping and a piping 15 which pressurizes by the insert gas, a liquid flow rate control device 10 which control flow rate of the compound 13 of the general formula (1) which is liquid, a vaporizer which vaporizes the compound 13 of the general formula (1) which is liquid, a piping 14 for supplying the inert gas in the PECVD equipment chamber via the vaporizer, and a gas flow rate control equipment 11 which controls flow rate of the insert gas. The vaporization equipment is connected to the upper electrode 3 equipped with a shower head from the vaporizer 9 via piping.

Figure 2:
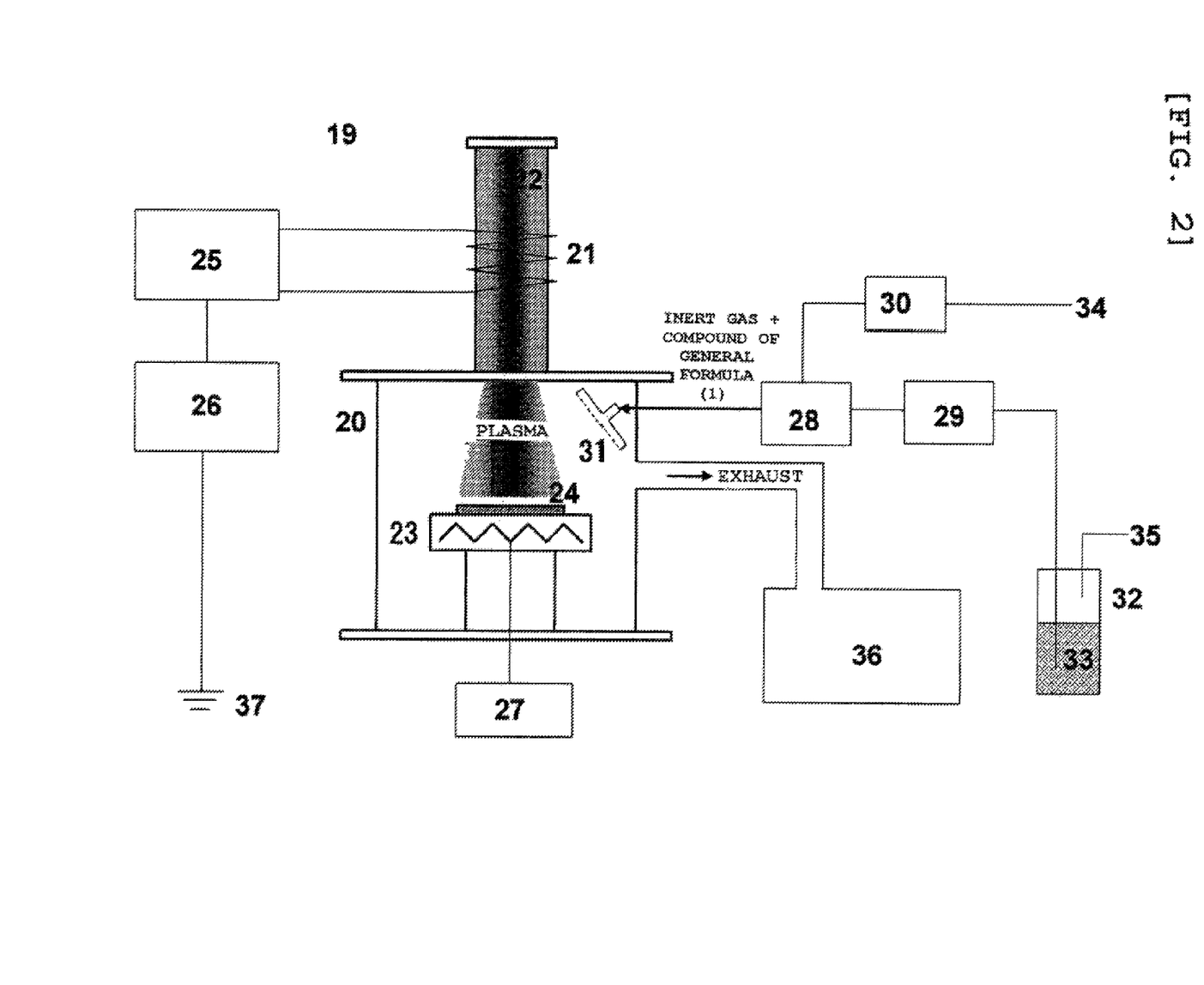
FIG. 2 is a view showing an inductively coupled PECVD equipment.

As one example of the PECVD equipment, an inductive coupled remote PECVD equipment is shown in FIG. 2. An inductive coupled remote PECVD equipment 19 shown in FIG. 2 comprises a plasma generation part wound in a coiled state around quartz at an upper portion of a PECVD equipment chamber, a temperature-controllable substrate setting part, a vaporization equipment which vaporizes the compound of the general formula (1) and supplies to the chamber, a plasma generation equipment comprising a high frequency power source and a matching circuit, and an exhaustion system comprising a vacuum pump.

Specifically, the PECVD equipment 19 comprises a PECVD chamber 20, a coil 21 and a quartz pipe 22 that are the plasma generation part, a heater part 23 for setting a thin film forming substrate 24 such as an Si substrate and a temperature control device 27, a vaporization equipment 28 to 35 for vaporizing the compound of the general formula (1), a matching circuit 25 and an RF power source 26, that are a plasma generation source, and an exhaust equipment 36 for exhausting an unreacted product and a by-product in the chamber. 37 is earth ground.

The coil around quartz as a plasma generation part is connected to the matching circuit 25, and discharge is conducted at an antenna current magnetic field by RF current in a quartz pipe to generate plasma. Standard of the RF power source 26 is not particularly limited, but the RF power source generally used in this technical field, having electric power of from 1 W to 2,000 W, and preferably from 10 w to 1,000 W, and a frequency of from 50 kHz to 2.5 GHz, preferably from 100 kHz to 100 MHz, and particularly preferably from 200 kHz to 50 MHz, can be used.

Control of a substrate temperature is not particularly limited, but the temperature is in a range of from −90 to 1,000° C., and preferably from 0° C. to 500° C.

The vaporization equipment comprises a container 32 filled with the compound 33 of the general formula (1) which is liquid at ordinary temperature and normal pressures and equipped with a dip piping and a piping 35 which pressurizes by the insert gas, a liquid flow rate control device 29 which controls flow rate of the compound 33 of the general formula (1) which is liquid, a vaporizer 28 which vaporizes the compound 33 of the general formula (1) which is liquid, a piping 34 for supplying the inert gas in the PECVD equipment chamber via the vaporizer, a gas flow rate control equipment 30 which controls flow rate of the insert gas, and a shower head 31 for uniformly supplying the inert gas and the gasified compound 33 of the formula (1) in the chamber.

The compound represented by the general formula (1) is gasified using, for example, the PECVD equipment as exemplified above, and supplied in the chamber, according to need, together with the inert gas, and is formed into a film by PECVD. In this case, pressure in the chamber is not particularly limited, but is from 0.1 Pa to 10,000 Pa, and preferably from 1 Pa to 5,000 Pa.

Thus, an Si-containing film is obtained. This film has a low dielectric constant, and depending on the conditions, a film having a dielectric constant of 2.0 or lower is obtained. Therefore, the film can be used as a low dielectric constant film. Further, the film preferably has a cyclic siloxane structure. The cyclic siloxane structure may be a residual cyclic siloxane structure in the cyclic siloxane compound represented by the general formula (1) or may be newly formed by plasma. As a result, a film having a cyclic siloxane structure is a porous film having a main pore size of 1 nm or less. Further, pores are not continuous, a metal does not diffuse in the film, and the film has high mechanical properties and high heat conduction. Therefore, the film is a thin film especially suitable as a low dielectric constant material (Low-k material) for semiconductor device. That is, it is further preferable that film formation is conducted under PECVD conditions so as not to disintegrate the cyclic siloxane structure in the cyclic siloxane compound represented by the general formula (1).

When the above Si-containing film is subjected to heat treatment, ultraviolet irradiation treatment or electron ray treatment, a porous thin film or a thin film having improved mechanical strength can be obtained. The Si-containing film having been subjected to those treatments in combination is included in the scope of the present invention. The thin film obtained by those treatments is suitable as a low dielectric constant insulating material.

The Si-containing films according to the present invention are all suitable as a low dielectric constant material, and those films can be used in a semiconductor device as an insulting film. In particular, those films are suitable in the production of ULSI using a multilayered interconnects.

Of the compounds represented by the general formula (1) of the present invention, particularly the compound represented by the general formula (20) is a novel compound. Here, $R^{18}$, $R^{19}$, g and h are the same as defined above. Preferably, $R^{18}$ is an alkyl group having from 1 to 6 carbon atoms, $R^{19}$ is an alkyl group having from 1 to 6 carbon atoms, g is 3 or 4, and h is 1 or 2, and more preferably, $R^{18}$ is an alkyl group having from 1 to 4 carbon atoms, and $R^{19}$ is an alkyl group having from 1 to 4 carbon atoms.

Specific examples of the compound represented by the general formula (20) include 2,4,6-triisopropyl-2,4,6-trimethyoxycyclotrisiloxane, 2,4,6-triisopropyl-2,4,6-triethyoxycyclotrisiloxane, 2,4,6-triisopropyl-2,4,6-tri-n-propoxycyclotrisiloxane, 2,4,6-triisopropyl-2,4,6-triisopropoxycyclotrisiloxane, 2,4,6-tris(methoxymethyl)-2,4,6-trimethylcyclotrisiloxane, 2,4,6,8-tetrakis (methoxymethyl)-2,4,6,8-tetramethylcyclotetrasiloxane, 2,4,6-tris(ethoxymethyl)-2,4,6-trimethylcyclotrisiloxane, 2,4,6,8-tetrakis-(ethoxymethyl)-2,4,6,8-tetramethylcyclotetrasiloxane, 2,4,6-tris(isopropoxymethyl)-2,4,6-trimethylcyclotrisiloxane, and 2,4,6,8-tetrakis(isoproxymethyl)-2,4,6,8-tetramethylcyclotetrasiloxane.

Further examples include 2,4,6-tris(methoxyethyl)-2,4,6-trimethylcyclotrisiloxane, 2,4,6,8-tetrakis(methoxyethyl)-2,4,6,8-tetramethylcyclotetrasiloxane, 2,4,6-tris-(ethoxyethyl)-2,4,6-trimethylcyclotrisiloxane, 2,4,6,8-tetrakis (ethoxyethyl)-2,4,6,8-tetramethylcyclotetrasiloxane, 2,4,6-tris(isopropoxyethyl)-2,4,6-trimethylcyclotrisiloxane, and 2,4,6,8-tetrakis(isopropoxyethyl)-2,4,6,8-tetramethylcyclotetrasiloxane.

The Examples are described below, but the invention is not limited by those Examples in any way. Film thickness was measured using an interferometric thin film measurement device, a product of Horiba, Ltd. Dielectric constant (k value) was measured using a mercury prober, a product of Four Dimensions Inc., and rigidity and Young's modulus were measured using a nanoindentater, a product of Hysitron Inc.

Example 1

Production of Organic Silane Compound Represented by General Formula (10)

26.7 g (2.20 mol) of metallic magnesium and 0.53 liter of dried tetrahydrofuran were charged in a 1 liter four-necked flask equipped with a dropping funnel and a stirring device under nitrogen stream, and cooled to 0° C. 187 g mol) of 4-bromoanisole was added dropwise to the flask over 5 hours while stirring. Reaction was conducted at room temperature for 3 hours to obtain a tetrahydrofuran solution of 4-methoxyphenyl magnesium bromide. 130 g (0.952 mol) of methyl trimethoxysilane and 52.0 ml of dried tetrahydrofuran were charged in a 2 liter four-necked flask equipped with a dropping funnel and a stirring device under nitrogen stream and cooled to 0° C. 1.00 mol of the tetrahydrofuran solution of 4-methoxyphenyl magnesium bromide prepared above was added dropwise to the flask over 1 hour while stirring, and reaction was conducted at room temperature for 4 hours. After completion of the reaction, a magnesium methoxide residue by-produced was removed by filtration, and a filtrate obtained was distilled under reduced pressure to obtain 106 g (0.501 mol) of methyl(4-methoxyphenyl)dimethoxysilane as the desired product. The yield was 52.6%.

Methyl(4-methoxyphenyl)dimethoxysilane isolated was analyzed by $^1$H-NMR, $^{13}$C-NMR and GC-MS, and the following results were obtained.

$^1$H-NMR; δ0.33 ppm (s, 3H, CH$_3$—Si), δ3.55 ppm (s, 6H, 2CH$_3$—O—Si), δ3.81 ppm (s, 3H, CH$_3$—O-Ph), δ6.93 to 6.94 ppm (m, 2H, Ph-H), δ7.55 to 7.56 ppm (m, 2H, Ph-H)

$^{13}$C-NMR; δ4.8 ppm (CH$_3$—Si), 50.7 ppm (CH$_3$—O—Si), 55.2 ppm (CH$_3$—O-Ph), δ113.9 ppm (Ph), δ125.0 ppm (Ph), δ135.8 ppm (Ph), δ161.5 ppm (Ph)

GC-MS; Mw=212, C$_{10}$H$_{16}$O$_3$Si

[Production of Cyclic Siloxane Compound Represented by General Formula (1)]

21.2 g (100 mmol) of methyl(4-methoxyphenyl)dimethoxysilane, 1.80 g (100 mmol) of pure water, 9.81 g (100 mmol) of sulfuric acid and 20 ml of tetrahydrofuran were charged in a 100 ml Schlenk flask, and reaction was conducted at room temperature for 1 hour under stirring. After completion of the reaction, THF and water were distilled away. An organic layer obtained was dried with a molecular sieve, and after distillation under reduced pressure, 2,4,6-tris(4-methoxyphenyl)-2,4,6-trimethylcyclotrisiloxane was obtained as the desired product. The yield was 11.3%, and the conversion of methyl (4-methoxyphenyl)dimethoxysilane was 33.8%.

2,4,6-Tris(4-methoxyphenyl)-2,4,6-trimethylcyclotrisiloxane isolated was analyzed by GC-MS, and the following results were obtained.

GC-MS; Mw=498, C$_{24}$H$_{30}$O$_6$Si$_3$

Example 2

Production of Cyclic Siloxane Compound Represented by the General Formula (1)

0.0141 g (0.0800 mmol) of palladium chloride and 20.5 g (640 mmol) of methanol were charged in a 50 ml Schlenk flask equipped with a stirring device and a dropping funnel and stirred. 4.81 g (20.0 mmol) of 2,4,6,8-tetramethylcyclotetrasiloxane was added dropwise from the dropping funnel at room temperature over 30 minutes. After completion of the dropwise addition, the resulting mixture was stirred at room temperature for 15 hours. After completion of the reaction, methanol was distilled away, Pd residue was filtered off with a glass filter, and 2,4,6,8-tetramethyl-2,4,6,8-tetramethoxycyclotetrasiloxane was obtained as the desired product. The yield by gas chromatography was 1.5%.

2,4,6,8-Tetramethyl-2,4,6,8-tetramethoxycyclotetrasiloxane isolated was analyzed by GC-MS, and the following results were obtained.

GC-MS; Mw=360, C$_8$H$_{24}$O$_8$Si$_4$

Example 3

Production of Cyclic Siloxane Compound Represented by General Formula (1)

13.62 g (0.100 mol) of methyl trimethoxysilane and 100 ml of toluene were charged in a 200 ml Schlenk flask equipped with a stirring device and a dropping funnel and stirred, and temperature was 80° C. 1.35 g of pure water was added dropwise from the dropping funnel at 80° C. over 10 minutes. After completion of the dropwise addition, the resulting mixture was stirred under reflux conditions for 2 hours. After completion of the reaction, toluene was distilled away, and 2,4,6,8-tetramethyl-2,4,6,8-tetramethoxycyclotetrasiloxane was obtained as the desired product. The yield was 4.6%, and the conversion of methyl trimethoxysilane was 13.8%.

2,4,6,8-Tetramethyl-2,4,6,8-tetramethoxycyclotetrasiloxane isolated was analyzed by GC-MS, and the following results were obtained.

GC-MS; Mw=360, C$_8$H$_{24}$O$_8$Si$_4$

Example 4

Production of Cyclic Siloxane Compound Represented by General Formula (1)

96.2 g (1.6 mol) of isopropanol and 0.740 g (0.80 mmol) of chlorotris(triphenylphosphine)rhodium (I) were charged in a 200 ml Schlenk flask equipped with a stirring device and a dropping funnel and stirred. 48.1 g (0.20 mol) of 2,4,6,8-tetramethylcyclotetrasiloxane was added dropwise from the dropping funnel at room temperature over 20 minutes. After completion of the dropwise addition, the resulting mixture was stirred under isopropanol reflux conditions for 4 hours. After completion of the reaction, isopropanol was distilled away, and 2,4,6,8-tetramethyl-2,4,6,8-tetrisopropoxycyclotetrasiloxane was obtained as the desired product. The yield was 54.9%.

2,4,6,8-Tetramethyl-2,4,6,8-tetraisopropoxycyclotetrasiloxane isolated was analyzed by GC-MS, and the following results were obtained.

GC-MS; Mw=472, C$_{16}$H$_{40}$O$_8$Si$_4$

Example 5

Production of Cyclic Siloxane Compound Represented by General Formula (1)

20.0 g (0.217 mol) of toluene and 2.4 g of 0.01N sulfuric acid aqueous solution were charged in a 200 ml Schlenk flask equipped with a stirring device and a dropping funnel and stirred. 20.0 g (0.133 mol) of methyl(methoxymethyl)dimethoxysilane was added dropwise from the dropping funnel at room temperature over 5 minutes. After completion of the dropwise addition, the resulting mixture was stirred at room temperature for 7 hours. After completion of the reaction, toluene was distilled away, and 2,4,6,8-tetrakis(methoxymethyl)-2,4,6,8-tetramethylcyclotetrasiloxane was obtained as the desired product. The yield was 15.3%, and the conversion of methyl-(methoxymethyl)dimethoxysilane was 61.2%.

2,4,6,8-Tetrakis(methoxymethyl)-2,4,6,8-tetramethylcyclotetrasiloxane isolated was analyzed by $^1$H-NMR, $^{13}$C-NMR and GC-MS, and the following results were obtained.

$^1$H-NMR; δ0.17 to 0.19 ppm (m, 12H, 4CH$_3$—Si) δ3.04 to 3.07 ppm (m, 8H, 4CH$_3$—O—CH$_2$Si) δ3.34 to 3.36 ppm (m, 12H, 4CH$_3$—O—CH$_2$Si)

$^{13}$C-NMR; δ-2.2 ppm (CH$_3$—Si) δ62.9 ppm (CH$_3$—O—CH$_2$Si) δ65.8 ppm (CH$_3$—O—CH$_2$Si)

GC-MS; Mw=416, C$_{12}$H$_{32}$O$_8$Si$_4$

Example 6

PECVD Film Formation Using Cyclic Siloxane Compound Represented by General Formula (1)

2,4,6-Tris(4-methoxyphenyl)-2,4,6-trimethylcyclotrisiloxane synthesized in Example 1 was film-formed on a silicon substrate using the capacitively coupled PECVD equipment shown in FIG. 1. The film formation conditions were that an argon gas as an inert gas is supplied at 10 sccm, vaporized 2,4,6-tris(4-methoxyphenyl)-2,4,6-trimethylcyclotrisiloxane was continued to supply such that a chamber inner pressure is 10 Pa, and a film is formed under the conditions that a substrate temperature is 150° C., RF power source power is 30 W, and RF power source frequency is 13.56 MHz. As a result, a film formation rate was 4.3 nm/min, and dielectric constant (k value) was a value of 2.7. Mechanical properties were that rigidity is 1.3 GPa and Young's modulus is 13.9 GPa.

Example 7

PECVD Film Formation Using Cyclic Siloxane Compound Represented by General Formula (1)

PECVD thin film was obtained in the same manner as in Example 6, except that 2,4,6,8-tetramethyl-2,4,6,8-tetramethoxycyclotetrasiloxane synthesized in Example 3 was used in place of 2,4,6-tris(4-methoxyphenyl)-2,4,6-trimethylcyclotrisiloxane. As a result, a film formation rate was 12.8 nm/min, and dielectric constant (k value) was a value of 2.6. Mechanical properties were that rigidity is 1.36 GPa and Young's modulus is 15.2 GPa.

Example 8

PECVD Film Formation Using Cyclic Siloxane Compound Represented by General Formula (1)

PECVD thin film was obtained in the same manner as in Example 6, except that 2,4,6,8-tetramethyl-2,4,6,8-tetraisopropoxycyclotetrasiloxane synthesized in Example 4 was used in place of 2,4,6-tris(4-methoxyphenyl)-2,4,6-trimethylcyclotrisiloxane. As a result, a film formation rate was 11.2 nm/min, and dielectric constant (k value) was a value of 2.4. Mechanical properties were that rigidity is 1.1 GPa and Young's modulus is 17.1 GPa.

Example 9

PECVD Film Formation Using Cyclic Siloxane Compound Represented by General Formula (1)

PECVD thin film was obtained in the same manner as in Example 6, except that 2,4,6,8-tetrakis(methoxymethyl)-2,4,6,8-tetramethylcyclotrasiloxane synthesized in Example 5 was used in place of 2,4,6-tris(4-methoxyphenyl)-2,4,6-trimethylcyclotrisiloxane. As a result, a film formation rate was 6.8 nm/min, and dielectric constant (k value) was a value of 1.8. Mechanical properties were that rigidity is 1.6 GPa and Young's modulus is 22.1 GPa.

Comparative Example 1

PECVD thin film was obtained in the same manner as in Example 6, except that 2,4,6,8-tetramethylcyclotetrasiloxane was used in place of 2,4,6-tris(4-methoxyphenyl)-2,4,6-trimethylcyclotrisiloxane. As a result, a film formation rate was 10.4 nm/min, and dielectric constant (k value) was a value of 2.9. Mechanical properties were that rigidity is 1.1 GPa and Young's modulus is 10.7 GPa.

While the invention has been described in detail and with reference to specific embodiments thereof, it will be apparent to one skilled in the art that various changes and modifications can be made therein without departing from the spirit and scope thereof.

This application is based on Japanese Patent Application (Patent Application No. 2005-023256) filed Jan. 31, 2005 and Japanese Patent Application (Patent Application No. 2005-349432) filed Dec. 2, 2005, the entire contents thereof being hereby incorporated by reference.

INDUSTRIAL APPLICABILITY

The present invention can provide a novel material for forming Si-containing film, especially a material for a low dielectric constant insulating film containing a cyclic siloxane compound suitable to PECVD equipment, and further provide an Si-containing film using the same and a semiconductor device containing those films.

The invention claimed is:

1. A material for forming Si-containing film, characterized by containing a cyclic siloxane compound represented by the following general formula (20)

[Chem. 2]

(20)

(In the formula, $R^{18}$ represents a hydrocarbon group, and $R^{19}$ represents a hydrogen atom or a hydrocarbon group. g is an integer of from 2 to 10, and h is an integer of from 1 to 3).

2. The material for forming Si-containing film as claimed in claim 1, characterized in that an amount of impurities other than silicon, carbon, oxygen, hydrogen, nitrogen and boron is less than 10 ppb, and a water content is less than 50 ppm.

3. A production method of an Si-containing film, characterized by using the material for forming Si-containing film as claimed in claim 1 as a raw material.

4. The production method as claimed in claim 3, characterized in that film formation is conducted by a chemical vapor deposition.

5. The production method as claimed in claim 4, characterized in that the chemical vapor deposition is a plasma enhanced chemical vapor deposition.

6. An Si-containing film, characterized by being obtained by the production method as claimed in claim 3.

7. The Si-containing film as claimed in claim 6, characterized by containing a cyclic siloxane structure in the cyclic siloxane compound represented by the general formula (20).

8. A production method of an Si-containing film, characterized by subjecting the Si-containing film as claimed in claim 6 to heat treatment, ultraviolet irradiation treatment or electron ray treatment.

9. An Si-containing film, characterized by being obtained by the production method as claimed in claim 8.

10. A semiconductor device, characterized by using the film as claimed in claim 6, as an insulating film.

11. A cyclic siloxane compound, characterized by being represented by the following general formula (20)

[Chem. 2]

(20)

(In the formula, $R^{18}$ represents a hydrocarbon group, and $R^{19}$ represents a hydrogen atom or a hydrocarbon group, g is an integer of from 2 to 10, and h is an integer of from 1 to 3).

12. The cyclic siloxane compound as claimed in claim 11, characterized in that the compound represented by the general formula (20) is 2,4,6-tris(methoxymethyl)-2,4,6-trimethylcyclotrisiloxane, 2,4,6,8-tetrakis(methoxymethyl)-2,4,6,8-tetramethylcyclotetrasiloxane, 2,4,6-tris(ethoxymethyl)-2,4,6-trimethylcyclotrisiloxane, 2,4,6,8-tetrakis(ethoxymethyl)-2,4,6,8-tetramethylcyclotetrasiloxane, 2,4,6-tris(isopropoxymethyl)-2,4,6-trimethylcyclotrisiloxane, 2,4,6,8-tetrakis(isopropoxymethyl)-2,4,6,8-tetramethylcyclotetrasiloxane, 2,4,6-tris(methoxyethyl)-2,4,6-trimethylcyclotrisiloxane, 2,4,6,8-tetrakis(methoxyethyl)-2,4,6,8-tetramethylcyclotetrasiloxane, 2,4,6-tris(ethoxyethyl)-2,4,6-trimethylcyclotrisiloxane, 2,4,6,8-tetrakis(ethoxyethyl)-2,4,6,8-tetramethylcyclotetrasiloxane, 2,4,6-tris(isopropoxyethyl)-2,4,6-trimethylcyclotrisiloxane or 2,4,6,8-tetrakis(isopropoxyethyl)-2,4,6,8-tetramethylcyclotetrasiloxane.

13. The material for forming Si-containing film as claimed in 1, characterized in that the compound represented by the general formula (20) is 2,4,6-tris(methoxymethyl)-2,4,6-trimethylcyclotrisiloxane, 2,4,6,8-tetrakis(methoxymethyl)-2,4,6,8-tetramethylcyclotetrasiloxane, 2,4,6-tris(ethoxymethyl)-2,4,6-trimethylcyclotrisiloxane, 2,4,6,8-tetrakis(ethoxymethyl)-2,4,6,8-tetramethylcyclotetrasiloxane, 2,4,6-tris(isopropoxymethyl)-2,4,6-trimethylcyclotrisiloxane, 2,4,6,8-tetrakis(isopropoxymethyl)-2,4,6,8-tetramethylcyclotetrasiloxane, 2,4,6-tris(methoxyethyl)-2,4,6-trimethylcyclotrisiloxane, 2,4,6,8-tetrakis(methoxyethyl)-2,4,6,8-tetramethylcyclotetrasiloxane, 2,4,6-tris(ethoxyethyl)-2,4,6-trimethylcyclotrisiloxane, 2,4,6,8-tetrakis(ethoxyethyl)-2,4,6,8-tetramethylcyclotetrasiloxane, 2,4,6-tris(isopropoxyethyl)-2,4,6-trimethylcyclotrisiloxane or 2,4,6,8-tetrakis(isopropoxyethyl)-2,4,6,8-tetramethylcyclotetrasiloxane.

* * * * *